(12) United States Patent
Vartanian et al.

(10) Patent No.: US 12,172,029 B2
(45) Date of Patent: *Dec. 24, 2024

(54) TEMPORALLY MODULATED MULTI-LED FOR ENHANCED SUBCONSCIOUS PHYSIOLOGICAL RESPONSES

(71) Applicant: THE REGENT OF THE UNIVERSITY OF MICHIGAN, Ann Arbor, MI (US)

(72) Inventors: Garen V. Vartanian, Ann Arbor, MI (US); Kwoon Y. Wong, Ann Arbor, MI (US); Pei-Cheng Ku, Ann Arbor, MI (US); Scott A. Almburg, Redford Township, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,134

(22) Filed: Feb. 10, 2022

(65) Prior Publication Data
US 2022/0161052 A1 May 26, 2022

Related U.S. Application Data

(63) Continuation of application No. 15/658,338, filed on Jul. 24, 2017, now Pat. No. 11,285,337.
(Continued)

(51) Int. Cl.
*A61N 5/00* (2006.01)
*A61N 5/06* (2006.01)

(52) U.S. Cl.
CPC .......... *A61N 5/0618* (2013.01); *A61N 5/0622* (2013.01); *A61N 2005/0626* (2013.01);
(Continued)

(58) Field of Classification Search
None
See application file for complete search history.

(56) References Cited

U.S. PATENT DOCUMENTS

| 5,259,380 A | 11/1993 | Mendes et al. |
| 6,602,245 B1 | 8/2003 | Thiberg |
| (Continued) | | |

FOREIGN PATENT DOCUMENTS

WO   WO-2010122446 A1 * 10/2010 ............ A61M 21/00

OTHER PUBLICATIONS

Katsuura et al., "Effects of blue pulsed light on human physiological functions and subjective evaluation", Journal of Physiological Anthropology, 31:1-5 (2012).

*Primary Examiner* — Sana Sahand
(74) *Attorney, Agent, or Firm* — MARSHALL, GERSTEIN & BORUN LLP

(57) ABSTRACT

A light source and a method of generating a light using the light source is disclosed. The light source is configured to produce a plurality of distinct colors in generating the light, one of the distinct colors falling within a blue spectral light band. A light controller modulates the spectral light produced by the plurality of distinct colors. The modulation provides melanopsin contrast in order to increase melanopsin responsiveness of a subject exposed to the generated light and maintains the color temperature, color quality, and color constancy experienced by the subject in a lit viewing environment within an acceptable range.

9 Claims, 26 Drawing Sheets

Related U.S. Application Data

(60) Provisional application No. 62/365,610, filed on Jul. 22, 2016.

(52) U.S. Cl.
CPC ............... *A61N 2005/0652* (2013.01); *A61N 2005/0663* (2013.01)

(56) References Cited

U.S. PATENT DOCUMENTS

| | | |
|---|---|---|
| 6,602,275 B1 | 8/2003 | Sullivan |
| 7,453,217 B2 | 11/2008 | Lys et al. |
| 7,520,634 B2 | 4/2009 | Ducharme et al. |
| 8,900,282 B2 | 12/2014 | Brawn |
| 2009/0281604 A1* | 11/2009 | De Boer ............... A61M 21/00 345/83 |
| 2011/0190854 A1 | 8/2011 | Sung |
| 2011/0301406 A1* | 12/2011 | Ehara ................... A61M 21/02 600/27 |
| 2012/0095534 A1* | 4/2012 | Schlangen ............ A61M 21/00 607/90 |
| 2013/0238060 A1 | 9/2013 | Nevins |
| 2014/0228914 A1* | 8/2014 | van de Ven .......... A61N 5/0618 607/88 |
| 2016/0325109 A1* | 11/2016 | Knaus .................... A61N 5/06 |

\* cited by examiner

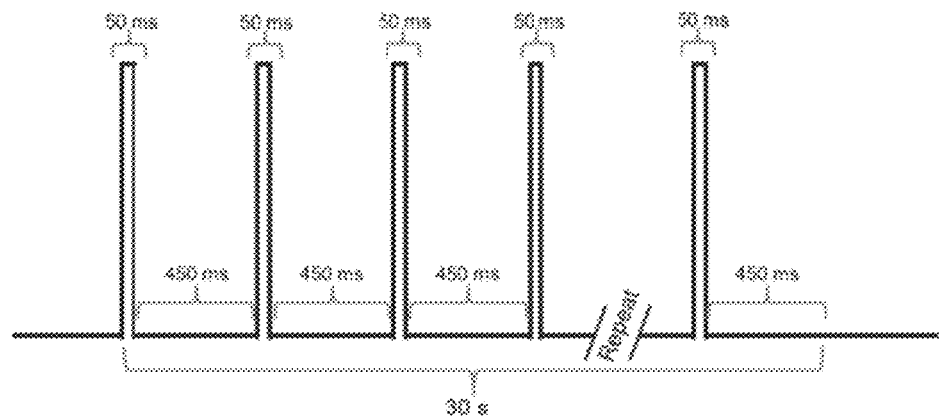
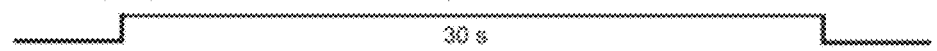
FIG. 3A
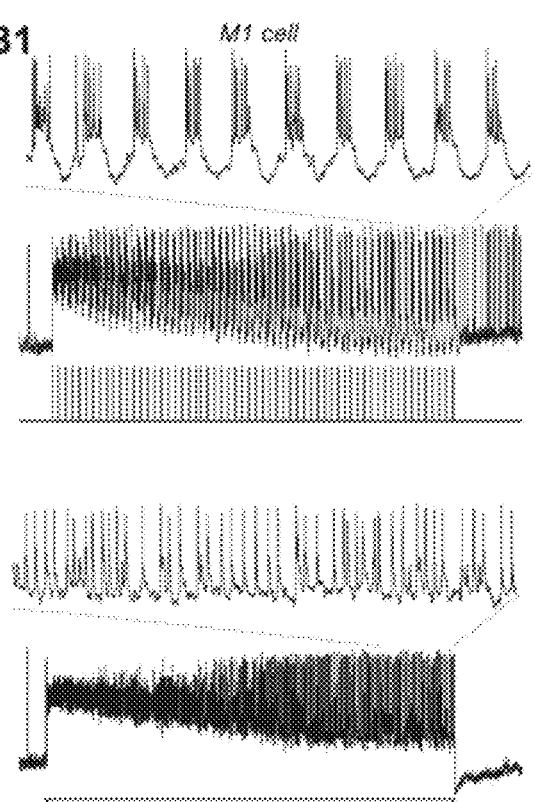
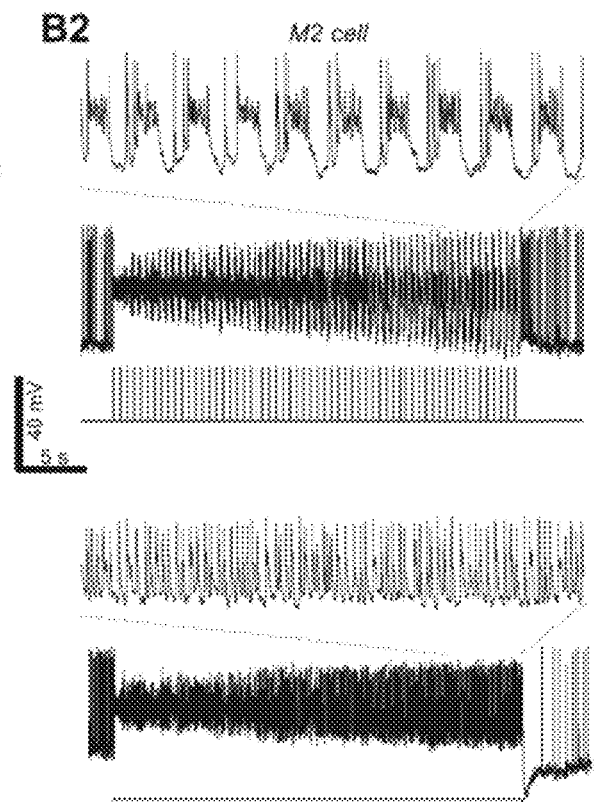
FIG. 3B1    FIG. 3B2

|  | $x_{10}, y_{10}$ | CCT | Michaelson contrast | Max/min ratio | Mean CII | CRI min | CRI max | CQS min | CQS max |
|---|---|---|---|---|---|---|---|---|---|
| General | (0.437, 0.404) | 3200 K | 4.7% | 1.10 | 1.22 | 79 | 85 | 64 | 72 |
| Therapeutic | (0.437, 0.404) | 3180 K | 30.1% | 1.86 | 8.18 | 65 | 80 | 37 | 68 |

FIG. 9

|  | Melanopsin-selective oscillating 5-LED light | Steady 5-LED light |
|---|---|---|
| Mean reaction time (lower is better): | 0.396 | 0.421 |
| Mean distractability (lower is better): | 0.0508 | 0.0620 |
| Mean error rate (lower is better): | 0.0479 | 0.0491 |

```
┌─────────────────────────────────────────────────┐
│     Providing a Plurality of LED Channels Including │
│        At Least Four Distinctly Colored LEDs        │
│                       102                           │
└─────────────────────────────────────────────────┘

┌─────────────────────────────────────────────────┐
│    Setting A First Light Mode at a First Spectrum To│
│         Maximally Stimulate Melanopsin Responsiveness,│
│    the First Spectrum Formed by Light from the At Least Four│
│       Distinctly Colored LEDs and Having a Light Intensity that│
│   Maximizes Melanopsin Contrast Responsiveness and Having│
│      a Blue Light Intensity, a Red Light Intensity, and/or a Green│
│          Light Intensity that Define a Color Temperature and│
│                Brightness of the First Light Mode         │
│                           104                             │
└─────────────────────────────────────────────────┘

┌─────────────────────────────────────────────────┐
│   Setting a Second Light Mode at a Second Spectrum to More│
│   Weakly Stimulate Melanopsin Responsiveness Compared to│
│     the First Light Mode, the Second Spectrum Formed by Light│
│    from the At Least Four Distinctly Colored LEDs and Having a│
│         Light Intensity that More Weakly Stimulates Melanopsin│
│    Responsiveness and Having a Blue Light Intensity, Red Light│
│      Intensity, and/or a Green Light Intensity that Define a Color│
│        Temperature and Brightness of the Second Light Mode│
│                           106                             │
└─────────────────────────────────────────────────┘

┌─────────────────────────────────────────────────┐
│  Setting the Color Temperature and the Brightness of the First│
│     Light Mode to Match the Color Temperature and Brightness│
│                   of the Second Light Mode                │
│                           108                             │
└─────────────────────────────────────────────────┘

┌─────────────────────────────────────────────────┐
│    Modulating Between the First Light Mode and the Second│
│              Light Mode While Maintaining an              │
│                Optimized Melanopsin Contrast              │
│                           110                             │
└─────────────────────────────────────────────────┘
```

FIG. 17

TEMPORALLY MODULATED MULTI-LED FOR ENHANCED SUBCONSCIOUS PHYSIOLOGICAL RESPONSES

CROSS-REFERENCE TO RELATED APPLICATION

This application is a continuation of U.S. patent application Ser. No. 15/658,338, now, U.S. Pat. No. 11,285,337, filed Jul. 24, 2017, and entitled "Temporally Modulated Multi-LED for Enhanced Subconscious Physiological Responses", which claims the benefit of the filing date of U.S. Provisional Patent Application No. 62/365,610, filed Jul. 22, 2016, and entitled "Temporally Modulated Multi-LED for Enhanced Subconscious Physiological Responses" and the entire contents thereof are incorporated by reference herein.

STATEMENT OF GOVERNMENT SUPPORT

This invention was made with government support under grant numbers EY013934 and EY007003 awarded by the National Institutes of Health. The government has certain rights in this invention.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Photic stimulation of retinal neurons evokes not only conscious vision but also subconscious responses central to our well-being. Because the average person spends >80% of their time indoors, the quality of artificial light has far-reaching health impacts. To date, lighting technologies have been designed to improve energy efficiency and visual comfort, but their physiological effects have been largely overlooked. Because the recommended illuminance of indoor lighting is typically ≥10-fold lower than outdoor levels, inadequate daytime light exposure has been linked to various morbidities.

The health impacts of light have been a topic of renewed interest recently, partly due to the recent discovery of a new class of photoreceptors: intrinsically photosensitive retinal ganglion cells (ipRGCs). ipRGCs sense light using the photopigment melanopsin which is most sensitive to 480 nm blue light. ipRGCs are the primary neurons mediating non-image-forming physiological responses to light, e.g., the pupillary light reflex, suppression of nocturnal melatonin release, and entrainment of circadian rhythms such as sleep to the light/dark cycle. As researchers are learning, insufficient daytime light exposure or overexposure during subjective night can result in not only discomfort but also jet lag symptoms, seasonal affective disorder (SAD), and general depressive disorders. Conversely, boosting daytime blue light exposure can decrease reaction times, increase alertness, and ameliorate SAD symptoms. But, as researchers are finding, it is unrealistic to promote subconscious photo-stimulation simply by enhancing blue emission in indoor lighting as that would cause poor color rendering and undesirable color temperature. Thus, having an alternative strategy to make indoor light more potent for subconscious visual stimulation would be highly advantageous.

SUMMARY OF THE INVENTION

Light is essential for not only visual perception but also the proper regulation of circadian rhythms, alertness and mood. These subconscious, non-image-forming visual responses are mediated by intrinsically photosensitive retinal ganglion cells (ipRGCs), which use the photopigment melanopsin to sense light. Pulsing light has been shown to reduce photoreceptor adaptation and therefore elicit stronger non-image-forming responses than constant light of comparable energy density.

The present techniques propose a new paradigm for general lighting that enhances subconscious visual stimulation, by introducing a melanopsin-selective flicker into the light through a silent substitution technique, which minimizes cone-based perception of the flicker.

In some examples, the techniques use a linear optimization algorithm, although numerous other mathematical optimization frameworks can be employed. The algorithm maximizes contrast of the subconscious, melanopsin-based response function while keeping conscious, cone driven responses to the pulsing light fixed. Additional boundary conditions utilize the lighting industry's standard test color samples (TCS) as an environmental mimic, as well as any specified object color, in order to limit the amount of perceived color change caused by the pulsing light within the viewing environment. For purposes of this application, the term "perceived color" refers to color temperature and brightness or luminosity, as well as other possible light qualities. With the present techniques, newly generated light can help overcome the detrimental effects of insufficient daytime light such as depression and sleep disorders.

In accordance with an example, a method of generating light using a light source comprises: generating lighting signals for controlling the light source, wherein the light source is configured to produce a plurality of distinct colors in generating the light, one of the distinct colors falling within a blue spectral light band; modulating the lighting signals to modulate the light produced by the plurality of distinct colors, the modulation being chosen to provide optimal melanopsin contrast in order to increase melanopsin responsiveness of a subject exposed to the light and the modulation being chosen to maintain color temperature and color quality within an acceptable range; and applying the modulated lighting signals to the light source and generating the light for increasing the melanopsin contrast responsiveness of the subject exposed to the light.

In accordance with another example, a light source comprises: a plurality of light source elements, each producing an output light at a different wavelength in the visible spectrum; and a light controller adapted to modulate one or more of the plurality of the light source elements, wherein the modulation increases melanopsin contrast responsiveness of a subject exposed to the generated light and the modulation maintains, within an acceptable range, color fidelity from the overall light output from the light source as experienced by a subject.

In accordance with another example, a method of adapting a pulsed light for general illumination comprises: providing a plurality of LED channels each generating light, the LED channels including at least four distinctly colored LEDs; setting a first light mode at a first spectrum to maximally stimulate melanopsin responsiveness of a subject, the first spectrum being formed by light from the at least four distinctly colored LEDs, the first light mode comprising a light intensity that maximizes melanopsin contrast responsiveness and a blue light intensity, a red light intensity, and/or a green light intensity that define a color temperature and brightness of the first light mode; setting a second light mode at a second spectrum to more weakly stimulate melanopsin responsiveness of the subject compared to the first light mode, the second spectrum being formed by light from the at least four distinctly colored LEDs, the second light mode comprising a light intensity that more weakly stimulates melanopsin responsiveness and a blue light intensity, red light intensity, and/or a green light intensity that define a color temperature and brightness of the second light mode; setting the color temperature and brightness of the first light mode to match the color temperature and brightness of the second light mode; and modulating between the first light mode and the second light mode to stimulate the subject while maintaining an optimized melanopsin contrast between the first light mode and the second light mode.

BRIEF DESCRIPTION OF THE DRAWINGS

FIGS. 3A-C illustrate responses of mouse ipRGCs to flickering versus steady lights with the stimuli presented shown in FIG. 3A, representative responses from an M1 cell and an M2 cell shown in FIGS. 3B1 and 3B2 respectively, and data averaged from all cells shown in FIG. 3C.

FIGS. 7A-1 illustrate trends in melanopsin contrast with relaxation of cone response constraints for a light with specified system parameters, with FIGS. 7A-7D illustrating responses to a system consisting of 5 LEDs and FIGS. 7E-7I illustrating melanopsin Michelson contrasts for simulations with 4, 5, 6, 10, and 400 LED channels, respectively.

FIG. 9 provides values of key lighting parameters for the general and therapeutic lights shown in FIGS. 8A,B.

FIG. 12 shows the results from a computer-based cognitive performance test.

FIG. 17 provides an exemplary method for adapting a pulsed blue light for general illumination.

DETAILED DESCRIPTION

Figure 1A:
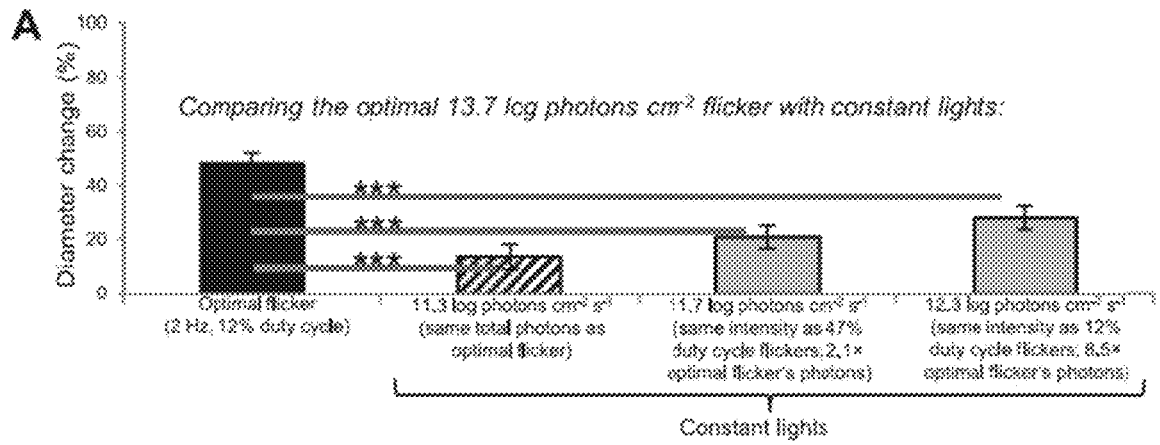
FIGS. 1A-C provide comparisons of human pupillary responses to flickering versus steady lights with black columns illustrating optimal flicker responses at three photon counts: 13.7 log photons $cm^{-2}$ (FIG. 1A), 14.7 log photons $cm^{-2}$ (FIG. 1B), and 15.7 log photons $cm^{-2}$ (FIG. 1C).
Figure 1B:
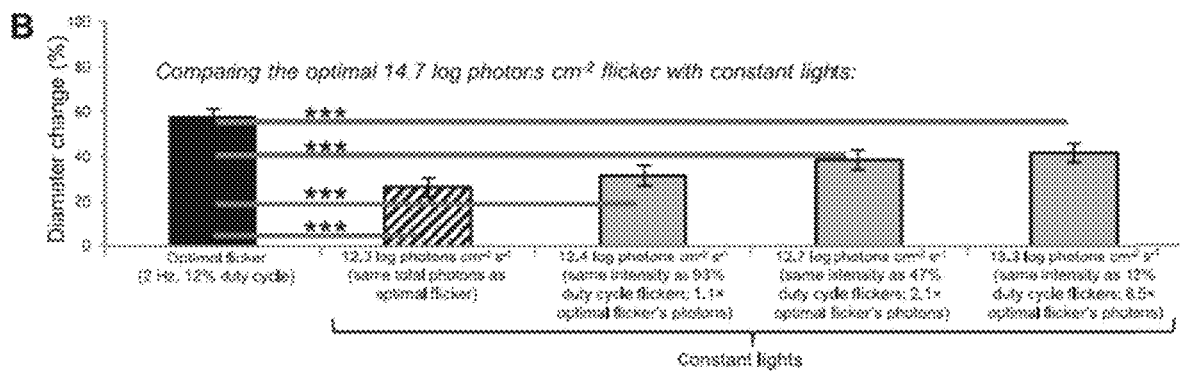
Figure 1C:
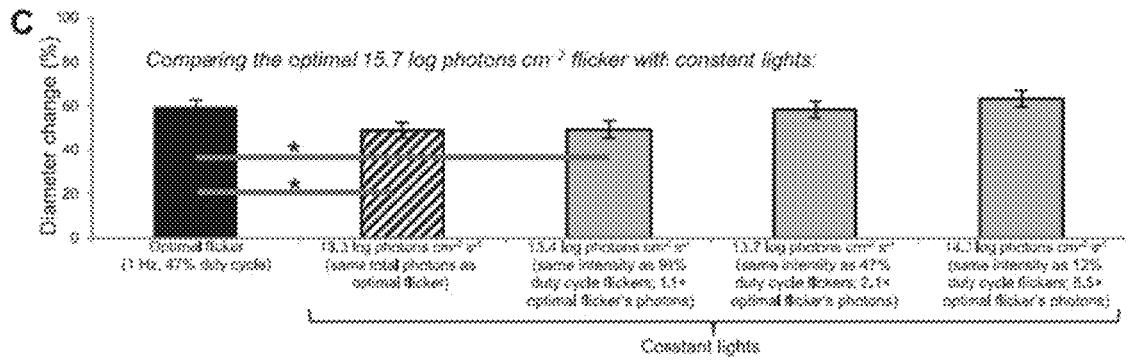

A detailed description of each of the figures and tables is provided first below, followed by a more general discussion of the relevant disclosure of this application. FIGS. 1-4 summarize empirical evidence that temporally flickering light stimulates ipRGCs more strongly than steady light. FIGS. 1A-C provide comparisons of human pupillary responses to flickering versus steady lights. The black columns illustrate optimal flicker responses at three photon counts: 13.7 log photons $cm^{-2}$ (FIG. 1A), 14.7 log photons $cm^{-2}$ (FIG. 1B), and 15.7 log photons $cm^{-2}$ (FIG. 1C). These flicker responses are compared with responses to steady lights that have either the same photon counts as the optimal flickers (hashed columns) or higher photon counts (gray columns). *$P<0.05$. ***$P<0.001$. Five subjects participated, each contributing two trials to all 14 conditions.

Figure 2A:
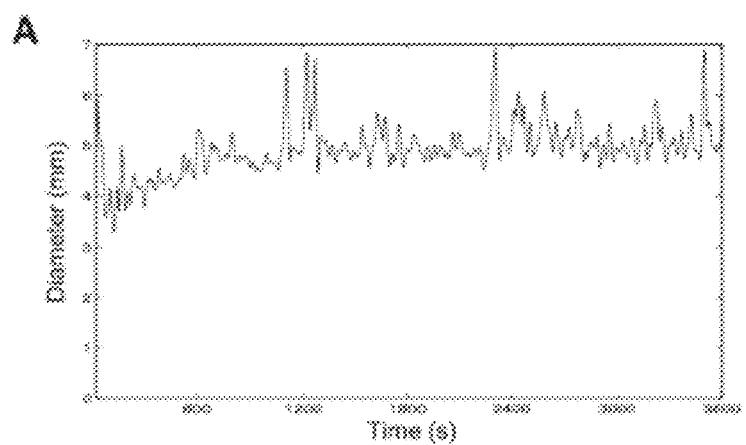
FIGS. 2A-B illustrate responses to prolonged photostimulation resulting from exposure to a 12.3 log photons $cm^{-2}$ constant light (FIG. 2A) or a 13.3 log photons $cm^{-2}$ $s^{-1}$ stimulus flickering at 2 Hz with a 12% duty cycle (FIG. 2B).
Figure 2B:
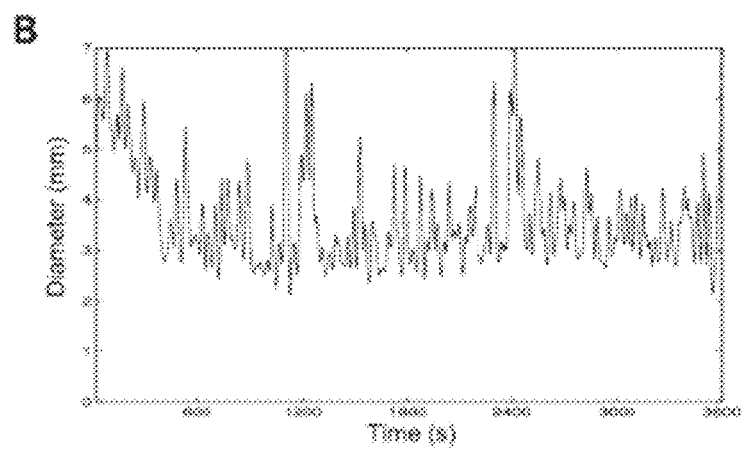

FIGS. 2A-B illustrate responses to prolonged photostimulation. After 60 minutes of dark adaptation, a subject was exposed to 60 minutes of either a 12.3 log photons $cm^{-2}$ constant light (as shown in FIG. 2A) or a 13.3 log photons $cm^{-2}$ $s^{-1}$ stimulus flickering at 2 Hz with a 12% duty cycle (as shown in FIG. 2B). In both cases, a total of 15.9 log photons $cm^{-2}$ was delivered per trial. Each trace was generated by averaging three trials. The steady-state pupillary response to the flicker (FIG. 2B) was significantly greater than that to the steady light (FIG. 2A).

Figure 3C:
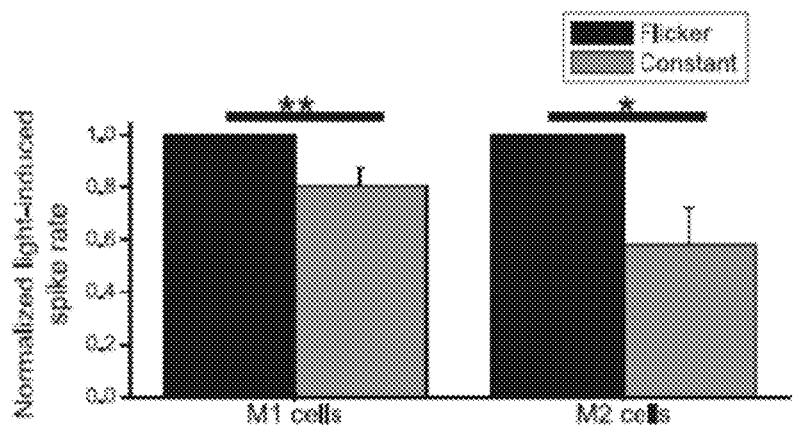

FIGS. 3A-C illustrate responses of mouse ipRGCs to flickering versus steady lights. Whole-cell current clamp recordings were made from 11 mouse ipRGCs (seven M1 cells and four M2 cells) under conditions that preserved synaptic input. Two stimuli (shown in FIG. 3A) were presented to each cell, in random order: a 12.9 log photons $cm^{-2}$ $s^{-1}$ light flickering at 2 Hz with a 10% duty cycle, and a steady 11.9 log photons $cm^{-2}$ $s^{-1}$ light with the same photon count as the flicker. All lights were full-field 440-nm light. Representative responses from an M1 cell are shown in FIG. 3B1 and representative responses from an M2 cell are shown in FIG. 3B2. The insets show magnified views of the final 5 seconds of the responses. FIG. 3C shows data averaged from all cells, illustrating that both ipRGC types displayed larger steady-state spiking responses to the flicker. *P<0.05. **P<0.01.

Figure 4:
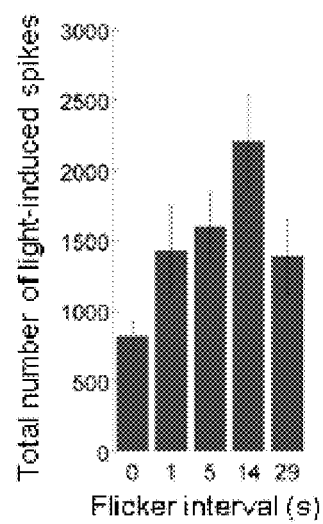
FIG. 4 illustrates spikes induced by twenty 1-s light pulses presented to rat ipRGCs during rod/cone signaling block at five intervals: 0 s (i.e. steady light), 1 s (0.5 Hz), 5 s (0.17 Hz), 14 s (0.07 Hz) and 29 s (0.03 Hz).

FIG. 4 depicts the results when twenty 1-s light pulses were presented to rat ipRGCs during rod/cone signaling block at five intervals: 0 s (i.e. steady light), 1 s (0.5 Hz), 5 s (0.17 Hz), 14 s (0.07 Hz) and 29 s (0.03 Hz). The 0.07 Hz flicker induced the most spikes, indicating that melanopsin responded more strongly to this flicker frequency than the steady light or the other three flicker frequencies.

Figure 5:
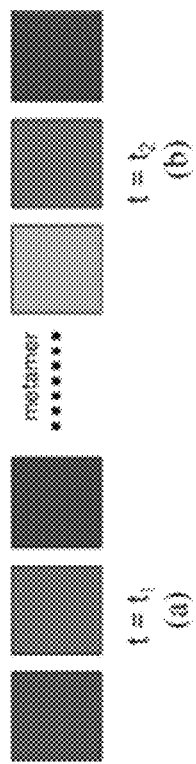
FIG. 5 illustrates a proposed scheme to incorporate a pulsed blue light in a white light source for general illumination.

FIGS. 5-10E summarize mathematical evidence that multi-LED lights containing melanopsin-targeted oscillations do not significantly distort human color vision. FIG. 5 illustrates a proposed scheme to incorporate a pulsed blue light in a white light source for general illumination. Since human beings see color using 3 distinct color-encoding photoreceptors (known as cones), it is possible to produce an infinite combination of 3 distinct color sources that when mixed appear to be the same color. As demonstrated in FIG. 5, two sets of distinct colors can appear to be the same (i.e. they are metamers) when optically mixed.

Figure 6:
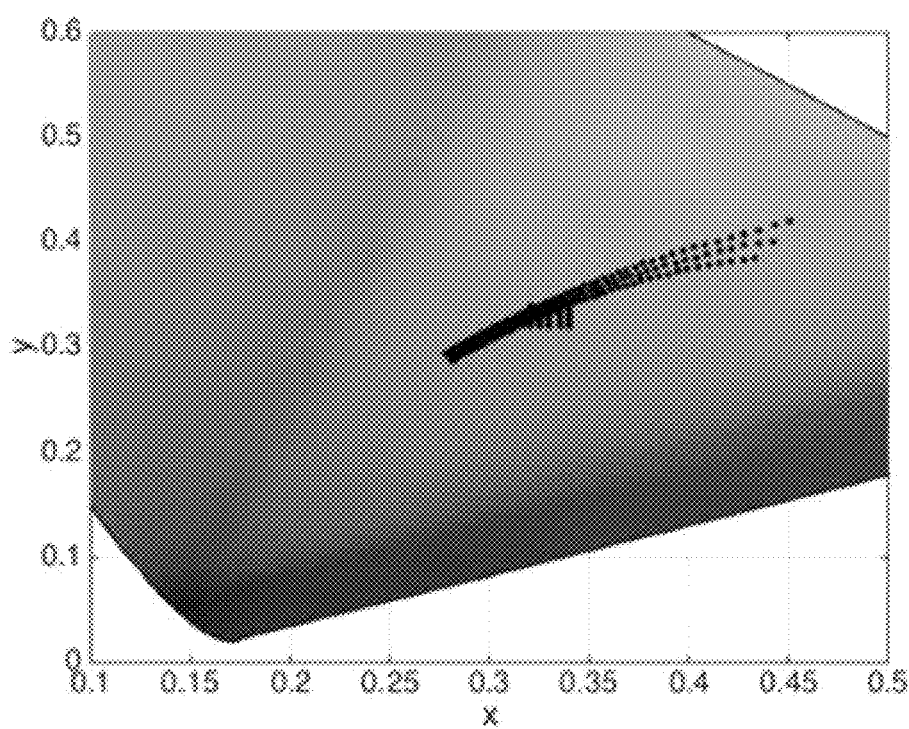
FIG. 6 illustrates suggested chromaticities to be explored as candidate lighting color specifications fall along the Planckian locus and its isotemperature lines from 3000 to 10000 K in small intervals as well as near and around the equi-energy point.
Figure 7B:
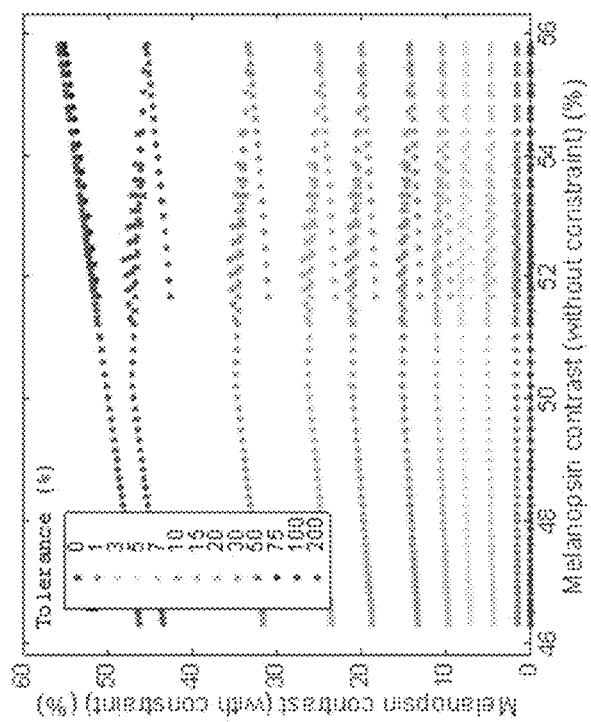
Figure 7A:
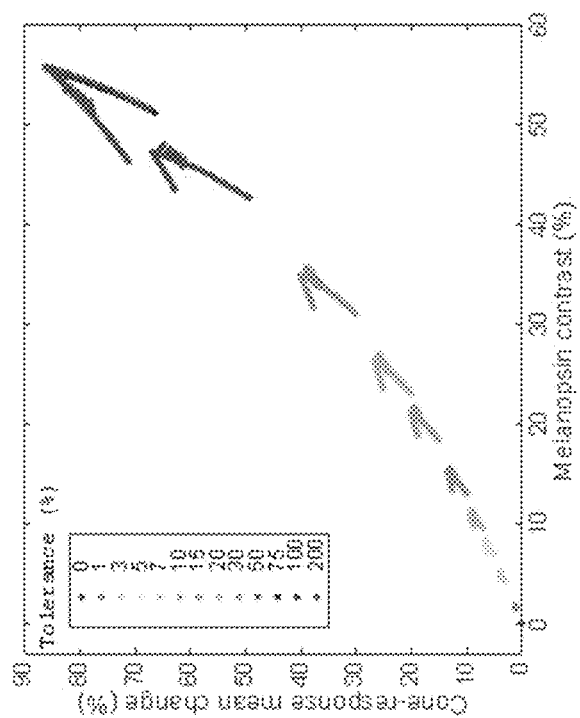
Figure 7D:
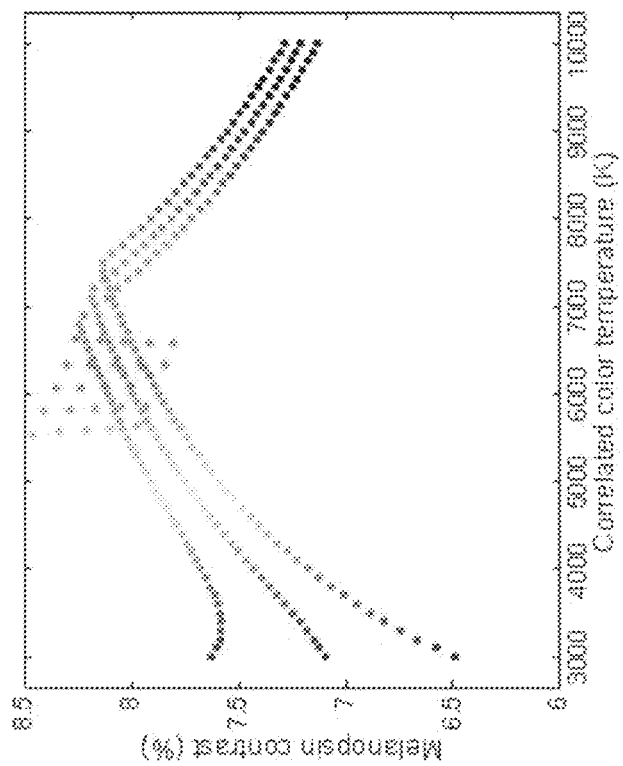
Figure 7C:
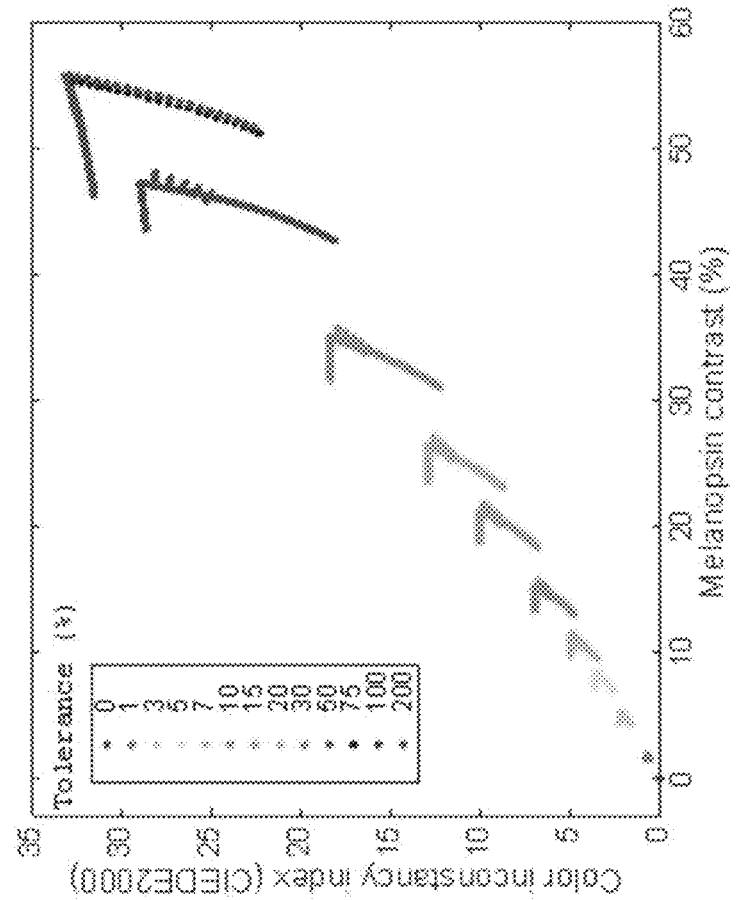
Figures 7E, 7F:
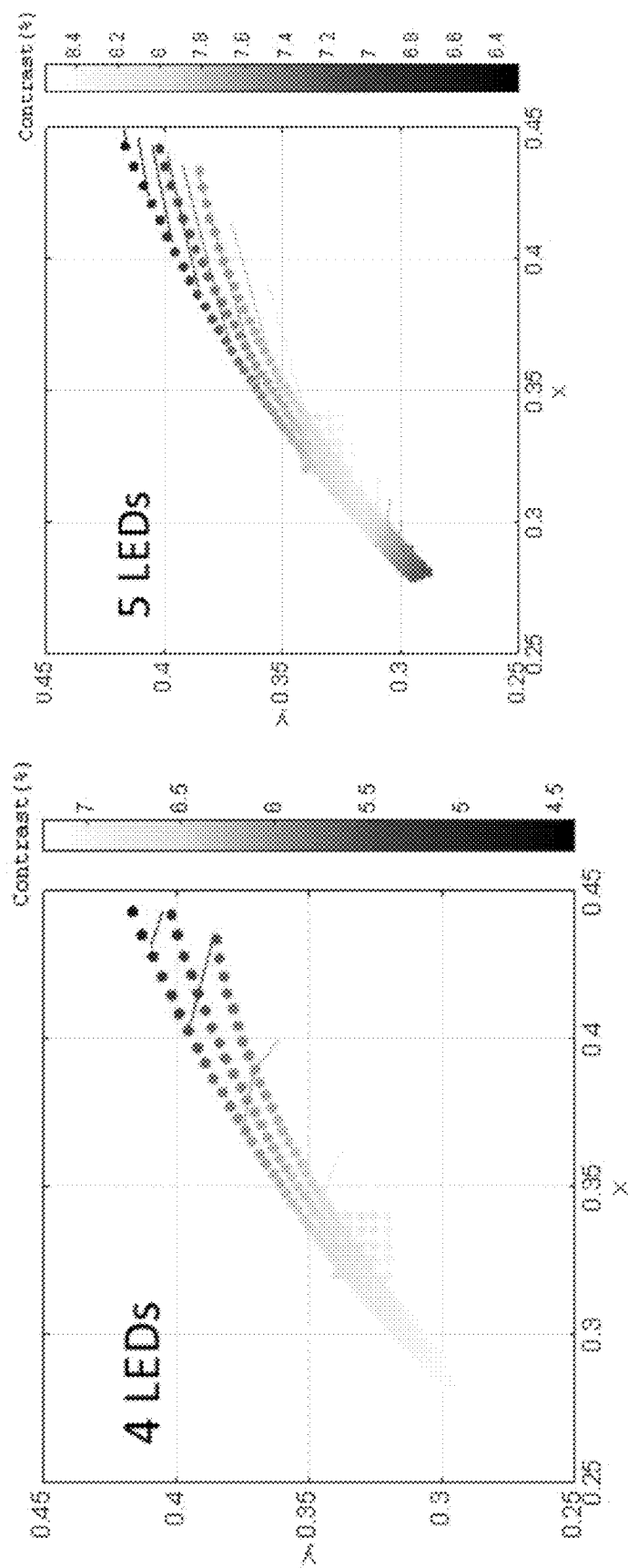
Figure 7H:
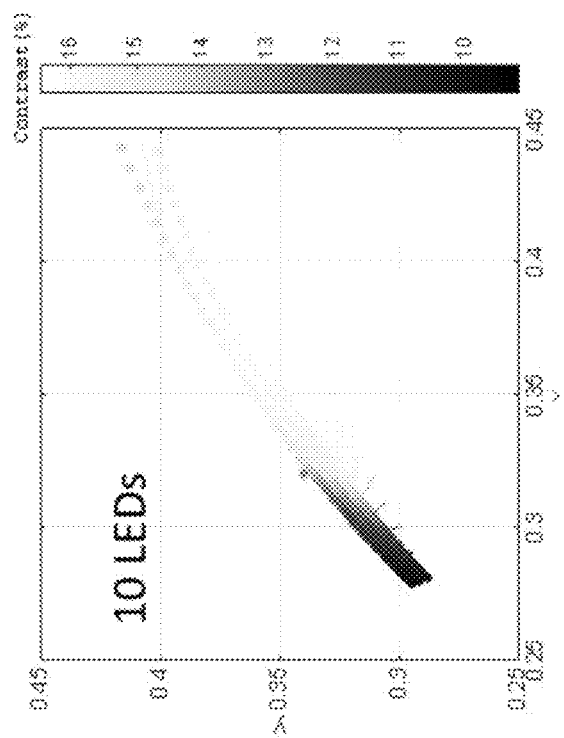
Figure 7G:
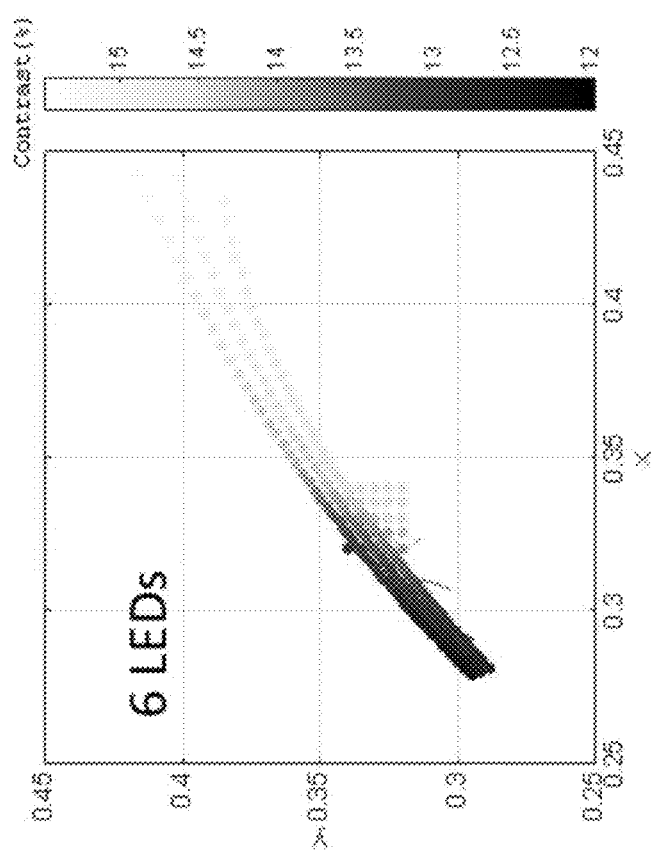
Figure 7I:
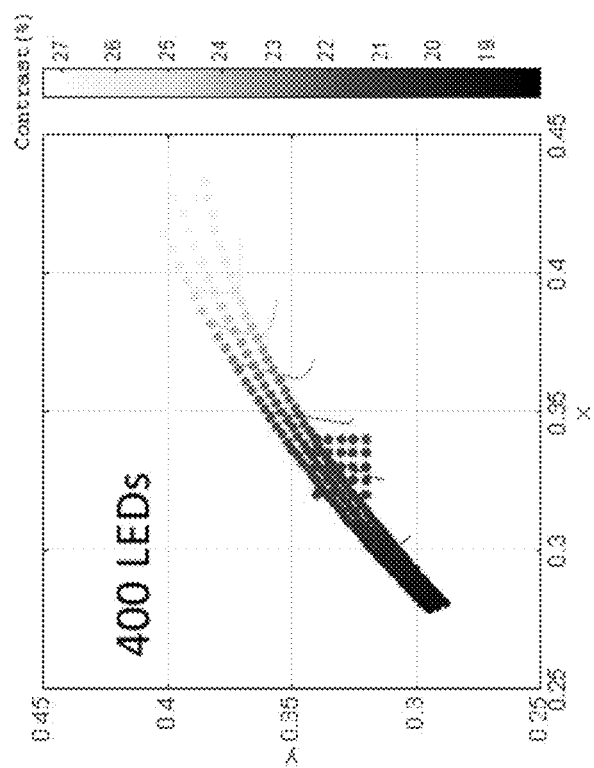

FIG. 6 illustrates suggested chromaticities to be explored as candidate lighting color specifications fall along the Planckian locus and its isotemperature lines from 3000 to 10000 K in small intervals-100 K intervals in the figure—as well as near and around the equi-energy point, i.e. a square bounded by (0.3203,0.3203) and (0.3403,0.3403). Sampled points are plotted here using the 10° response functions of the 1964 supplemental observer.

FIG. 7 illustrates survey of trends in melanopsin contrast with relaxation of cone response constraints for a light with specified system parameters. In FIGS. 7A-7D, the system consists of 5 LEDs (peak wavelengths 456, 488, 540, 592 and 632 nm; 10 nm full width at half maximum) with color coordinates along the Planckian locus, and the cone response change is calculated with respect to the oscillation of white light between the maximum-melanopsin spectra and minimum-melanopsin spectra. When calculating cone response changes in this case, the first 8 TCSs from the CRI standards are used. The tolerance to change in cone response ranges from 0% to 200%. As tolerance is increased, the optimized melanopsin contrast increases with mean cone response changes increasing concomitantly (FIG. 7A), ultimately matching the unconstrained contrast as tolerance approaches 200% (FIG. 7B). However, CII also increases as tolerance goes up (FIG. 7C). Melanopsin contrast reaches a maximum at 7000 K correlated color temperature (FIG. 7D). FIGS. 7E-7I illustrate melanopsin Michelson contrasts for simulations with 4, 5, 6, 10, and 400 LED channels, respectively, plotted on the CIE chromaticity diagram using 10° cone fundamentals. The correlated color temperature of maximum contrast shifts when the number of independent LED channels is adjusted. In FIGS. 7D-7I, isotemperature results are presented, as seen by the 3 contour-matched scatter plot groupings in each panel.

FIG. 8 provides spectra and metrics for general and therapeutic lighting. FIGS. 8A and 8B illustrate spectra of two example light sources with different applications: general lighting (FIG. 8A) and therapeutic lighting (FIG. 8B). FIGS. 8C and 8D illustrate individual CII values for 14 TCSs specified in CRI calculations for the general (FIG. 8C) and therapeutic (FIG. 8D) light sources. FIGS. 8E and 8F illustrate the amount of cone response change to the first 8 TCSs, as spectra oscillate between the maximum- and minimum-melanopsin states for general (FIG. 8E) and therapeutic (FIG. 8F) lights.

FIG. 9 provides values of key lighting parameters for the general and therapeutic lights shown in FIG. 3. "CCT": the correlated color temperature of the illuminant. "Max/min ratio", the ratio of the melanopsin response induced by the maximum- vs. the minimum-melanopsin spectrum. "Mean CII", the average color inconstancy index with respect to all 14 TCSs. "CRI min", "CRI max", "CQS min" and "CQS max", the color rendering index and color quality scale values of the minimum- and maximum-melanopsin illuminants.

FIGS. 10A-10E illustrate mean CII vs. melanopsin contrast as TCS boundary conditions are expanded for lights with 4, 5, 6, 10, and 400 independent LED channels, respectively. TCS 9-12 are high chroma red, yellow, green, and blue colors respectively, which are excluded from the calculation of general CRIB but are regularly encountered in real life. In the legend, "first 8" refers to the inclusion of the first 8 TCSs in the constraint matrix, "first 8+9th" means including the first 8 TCSs plus the 9th TCS, etc. The panels reveal trends toward reduced CII and contrast as additional TCSs are included in the constraints. Including TCS 12 (strong blue) in the boundary conditions shows the largest drop in melanopsin contrast, often with little benefit to reduction in mean CII.

Figure 11:
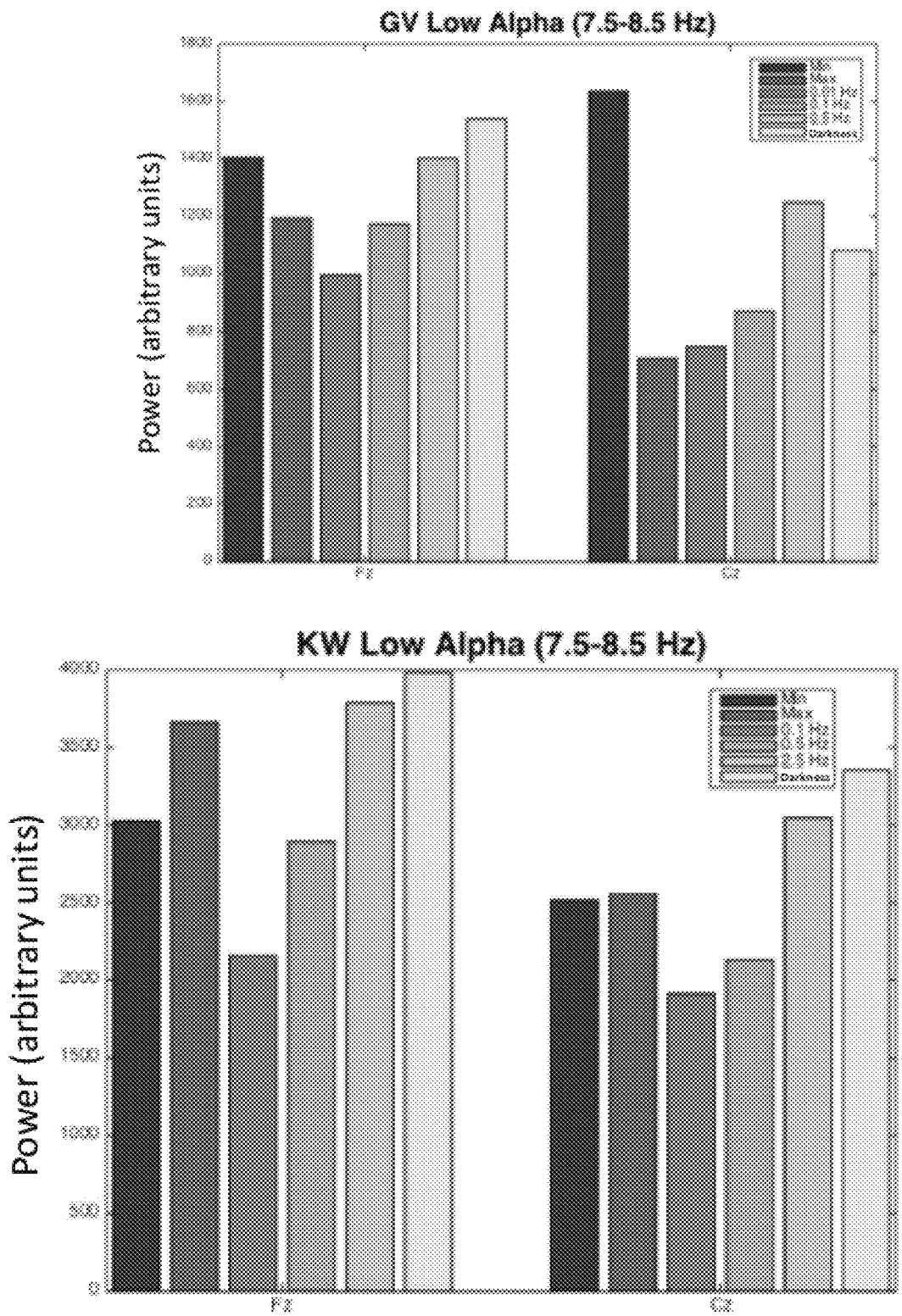
FIG. 11 illustrates electroencephalograms (EEGs) that were recorded from two subjects (GV and KW) using two scalp electrodes (Fz and Cz), while each person was viewing the 5-LED light source presenting 6 different stimuli.

FIG. 11 and FIG. 12 summarize empirical evidence that multi-LED lights containing melanopsin-targeted oscillations enhance alertness and cognitive performance in humans. In FIG. 11, electroencephalograms (EEGs) were recorded from two subjects (GV and KW) using two scalp electrodes (Fz and Cz), while each person was viewing the 5-LED light source presenting 6 different stimuli. "Min": a steady minimum-melanopsin stimulus designed to excite melanopsin weakly. "Max": a steady maximum-melanopsin stimulus that excites melanopsin strongly. "0.01 Hz", "0.1 Hz", "0.5 Hz" and "2.5 Hz": melanopsin-isolating stimuli that oscillate sinusoidally between the min and max states at the stated frequencies. "Darkness": the light was turned completely off. A reduction in low alpha power indicates an increase in alertness.

FIG. 12 shows the results from a computer-based cognitive performance test. This experiment was performed on three subjects, who were randomly selected students. In each session, a subject was comfortably seated while reading a book for 1 hour under either the melanopsin-selective oscillating light, the minimum-melanopsin steady light, or the maximum-melanopsin steady light. The subjects were not told the expected effects of the lighting conditions. In total, the subjects were tested under the oscillating light 10 times and the steady lights 12 times. The data from all subjects were averaged and the oscillating light was found to be superior to the steady lights in all three parameters measured: reaction time, distractability, and error rate.

The last five figures present example strategies to implement the multi-LED lighting technology disclosed herein, as discussed in greater detail below after a broader discussion of the disclosure of the present application.

Temporally modulated light stimulates the subconscious visual system more effectively than constant light. For both ipRGCs and downstream targets such as the central circadian pacemaker, melanopsin-based responses to constant light adapt within seconds. Thus, an intermittently varying light intensity reduces melanopsin adaptation and enhances ipRGC responses, ultimately stimulating cognitive brain activity.

In a human study, we systematically tested many light flickers of different intensities, duty cycles and flicker frequencies, as well as many steady light stimuli of various intensities, and found that the optimal flickers always caused greater pupil constrictions than steady lights containing the same total number of photons, as shown in FIGS. 1 and 2. Remarkably, even when the intensities of the steady lights were increased by up to 10-fold, these optimal flickers still caused greater steady-state pupil constrictions, as summarized in FIG. 1. Because prior primate research had demonstrated a tight correlation between the pupillary light reflex and ipRGC spiking activity such that a higher ipRGC spike rate leads to a greater pupil constriction, we can infer from the FIG. 1 and FIG. 2 results that flickering light is far more effective than constant light for stimulating human ipRGCs. Confirming this result, electrophysiological recordings from individual mouse ipRGCs showed that flickering light induces more action potentials (also known as "spikes" or "impulses") than steady light containing the same photon count, as summarized in FIG. 3. This trend was observed in both M1 and M2 types of mouse ipRGCs, which are analogous to the two types of ipRGCs present in the human retina.

The above experiments were conducted under conditions preserving rod/cone input to ipRGCs, i.e. ipRGCs responded to light not only directly via melanopsin but also indirectly via the rod and cone photoreceptors. In the experiment shown in FIG. 4, we made spike recordings from individual rat ipRGCs under pharmacological conditions that blocked rod/cone signaling, so that melanopsin-based light responses could be measured in isolation. Twenty 1-s light pulses were presented at five intervals: 0 s (i.e. steady light), 1 s (0.5 Hz), 5 s (0.17 Hz), 14 s (0.07 Hz) and 29 s (0.03 Hz). All four flickers evoked more spikes than the steady light, indicating that melanopsin responds better to flickering light than steady light. Moreover, the 0.07 Hz flicker induced more spikes than the other three flicker frequencies, suggesting that the best frequency for stimulating melanopsin is between ~0.05 and ~0.15 Hz.

Given that melanopsin is most sensitive to blue light and that ipRGCs respond better to flickering light than to steady light, one way of making daytime interior lighting healthier is by incorporating temporally modulated blue light into electric lights. However, this hypothetical light source is not practical because of the presence of a strong blue hue and because periodic fluctuation would create a very unpleasant visual experience. Thus, we developed a novel lighting technology incorporating a technique called silent substitution to create a blue light that flickers subconsciously. In this technique, the spectral contents of light are shifted in such a coordinated way that the shift selectively changes the activity of just one photopigment while leaving all other photopigments unaffected.

In some examples, the present techniques include using a light source having 4 differently colored LED channels: a blue channel tuned to melanopsin's peak sensitivity, and 3 additional channels with shorter and longer wavelengths. The non-blue channels offset the blue channel to create a visually appealing warm white appearance, and the 4 channels are modulated according to the silent substitution method so that the temporal fluctuation is detected only by ipRGCs' subconscious photopigment melanopsin but not by cone or rod photoreceptors; thus, the light is perceived by the viewer as a steady light.

In some examples, the present techniques include using a light source having 4 differently colored LED channels such as that depicted in FIG. 5: a first blue channel tuned to melanopsin's peak sensitivity (i.e., at or near 480 nm), a second spectrally non-redundant blue channel tuned to a wavelength triggering a weaker melanopsin response (i.e., farther from 480 nm), a green channel and a red channel. The two blue channels are turned on alternately. The intensities of the green and red channels are temporally modulated to compensate for the differences of the two blue channels. That is, the spectrum of the white light output is oscillated between two spectral states, one maximally and one minimally stimulating melanopsin. The four channels are modulated according to the silent substitution method so that the temporal fluctuation is detected only by ipRGCs' subconscious photopigment melanopsin but not by cone or rod photoreceptors, so that the light is perceived by the viewer as a steady light.

The present techniques incorporate temporally modulated blue light into an electric light thereby boosting subconscious responses at a typical indoor illuminance level. However, a proper compensation scheme is needed to mask the periodic intensity fluctuation. When temporally modulating the blue component in a white light, two sources of perceived fluctuation are generated: temporal variations in the color coordinates of the light source itself and scenery variations of the illuminated environment. With the present techniques, we show that by using multiple independently modulated color channels, the silent substitution technique, and mathematical optimizations, the sources of visible flickering can be minimized, while maintaining the beneficial effects for ipRGC targets.

Since conscious vision is primarily mediated by cone photoreceptors under daytime lighting conditions, two stimuli with dissimilar spectral power distributions can still look identical to an observer if both spectra produce equivalent responses among the 3 cone channels. Such spectra are called cone metamers. When one metamer is substituted with another, no change in the cone response is evoked; this process is called silent substitution.

The present techniques extend the metamer concept and introduce four or more color channels implemented using light sources, such as LEDs. When the channel that most strongly stimulates melanopsin is temporally modulated, the other channels are simultaneously modulated such that the overall cone-based color coordinates remain constant. In this way, the proposed light source may periodically oscillate between two cone metamers: one that stimulates melanopsin the most ("maximum melanopsin") and another that stimulates it the least ("minimum melanopsin"). To minimize the environmental flickering, we searched within the "maximum melanopsin" and "minimum melanopsin" solutions such that the pair of spectra generates the least spectral reflection shifts from standardized test color samples (TCS).

In confirming our results, the shift in cone excitation was calculated as a Weber contrast (i) for each TCS and (ii) for each of the 3 cone responses (short-, mid- and long-wavelength), by integrating the maximum melanopsin spectrum with the cone responses and taking the difference from the value for the minimum melanopsin spectrum.

To further measure the perceived shift in color when alternating between the two spectra, a color inconstancy index (CII) was applied for each TCS and averaged. Here we used the CIE color difference equation (2000), CIEDE2000.

Color inconstancy is typically calculated to gauge the degree of color fidelity of a color sample with a change in illuminant. In this case, we estimated the inconstancy of the scene as the lighting spectrum oscillates between the minimum and maximum melanopsin spectra.

To calculate the CII, we first applied a chromatic adaptation transform for both minimum and maximum melanopsin spectra with respect to the reference illuminant best suited for use with CIEDE2000. Since this difference equation operates on the basis of CIELAB, the reference illuminant is D65 with an illuminance level of 1000 lux. The adaptation transform was used for the index to correlate with visual evaluation. The selected transform was CAT02 with sharpened cone fundamentals; it is the most recent recommendation from CIE and can be found in the CIECAM02 specifications.

The TCS spectral reflectances were integrated with the spectral profile of first the minimum-melanopsin and then the maximum-melanopsin illuminant and tristimulus values were calculated. The transform was applied in order to calculate corresponding color coordinates for TCS reflectances under the reference illuminant. Once the corresponding color coordinates under the reference illuminant were specified for a TCS under minimum- and maximum-melanopsin conditions, a CII was calculated.

The number of color channels, e.g., the number of LED channels can vary. We discuss herein specific examples of 4 LED channels and 5 LED channels. However, any number of color channels may be used with corresponding increases in the controller operation when determining color separation and minimum-melanopsin and maximum-melanopsin responses.

Figure 8B:
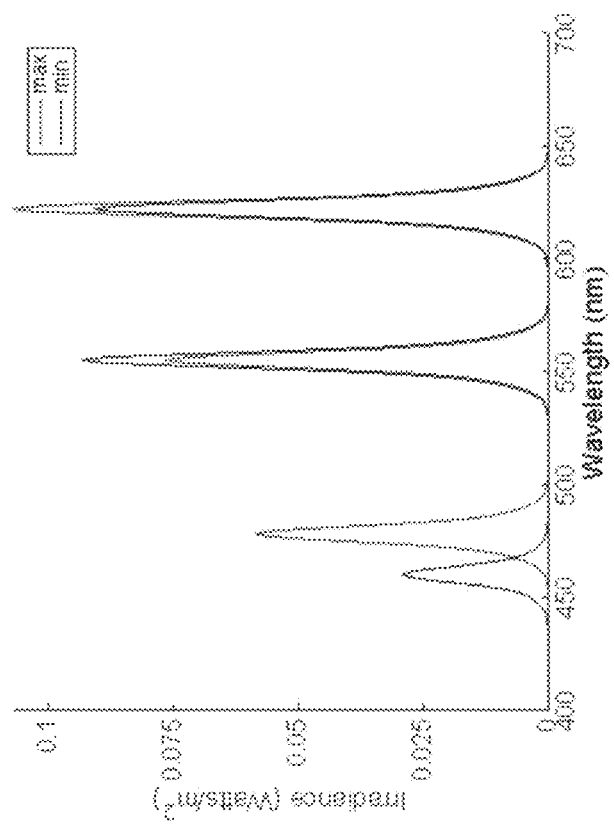
FIGS. 8A-F illustrate spectra and metrics for general and therapeutic lighting with FIGS. 8A and 8B illustrating spectra of two example light sources for general lighting (FIG. 8A) and therapeutic lighting (FIG. 8B), FIGS. 8C and 8D illustrating individual CII values for 14 TCSs specified in CRI calculations for the general (FIG. 8C) and therapeutic (FIG. 8D) light sources, and FIGS. 8E and 8F illustrating the amount of cone response change to the first 8 TCSs, as spectra oscillate between the maximum- and minimum-melanopsin states for general (FIG. 8E) and therapeutic (FIG. 8F) lights.
Figure 8A:
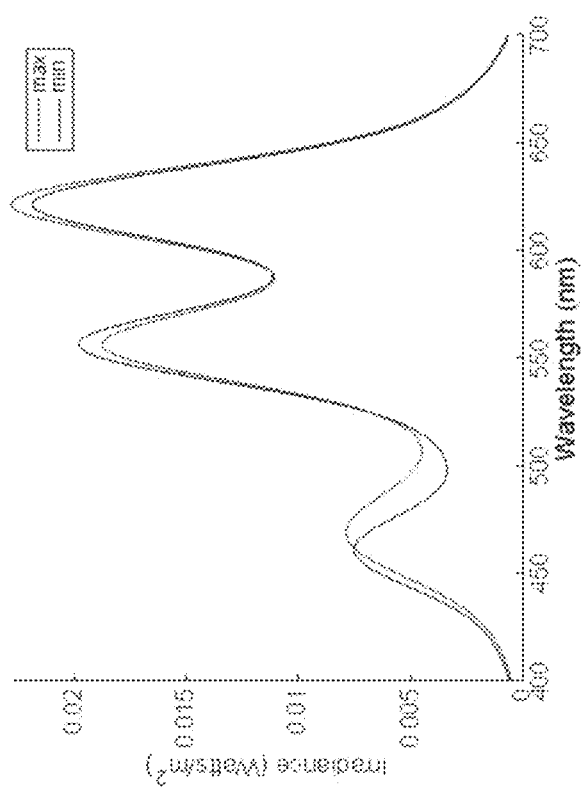

In examining sample optimum conditions, we varied the number of LED channels from 4 to 400 and the spectral full width at half maximum (FWHM) from 1 nm to 100 nm. We also varied the maximum allowable shift in cone response between the maximum and minimum melanopsin spectra. A small tolerance in the cone shift was used for the light source to be suitable for general illumination (FIG. 8A), whereas this constraint can be greatly relaxed for a therapeutic light source (FIG. 8B).

In these examples, we considered white light sources along the Planckian locus and its isotemperature lines with color temperatures ranging from 3000 to 11000 K in 100 K intervals (FIG. 6). For each condition, we calculated the color rendering index (CRI), color quality scale (CQS), and CII. The CII value provided an approximate quantity for predicting "just noticeable differences" in color. A CII of 1 describes a barely perceptible color difference in side-by-side sample comparisons by an average viewer, while larger values reflect greater, more readily perceived color differences. FIG. 7 summarizes the results for an illuminant system containing 5 LEDs, each with a 10 nm FWHM. To facilitate discussions, we focus on three tolerance levels in FIG. 8: no constraints, 50% tolerance, and 5% tolerance. The first case is relevant to phototherapeutic devices while the others have potential applications in general lighting.

We found that there is a tradeoff between melanopsin contrast and illuminant quality measured by CRI (or CQS) and CII. As expected, the highest melanopsin contrast can be obtained when there is no constraint on the tolerable cone response shift between the two spectra. When the maximum number (400) of LED channels was used for example, the highest melanopsin contrast was achieved: a Michelson contrast of 87.4%, corresponding to a maximum-to-minimum melanopsin response ratio of 14.9. However, this system also produced the lowest (poorest) CRI and CQS values: the CRI of the maximum and minimum spectra oscillates between −26 and −306, and the CQS value is 0 for both spectra. The mean CII is 34, which will produce an obviously fluctuating and hence unpleasant lighting environment. In short, the melanopsin effect can be maximized, but designers should also consider the effect on color rendering of the resulting affected light.

In other tests, we examined for the smallest CRI shift, noting that many conditions from our iteration qualify with little change in CRI value. These conditions can also demonstrate high melanopsin contrasts. For example, a 6-LED system with a tolerance of ±50% and FWHM of 10 nm has a contrast of 47%. However, CRI values for such as system can be very low, in this case 33, with CII at 16 and CQS oscillating between 9 and 32.

Figure 8D:
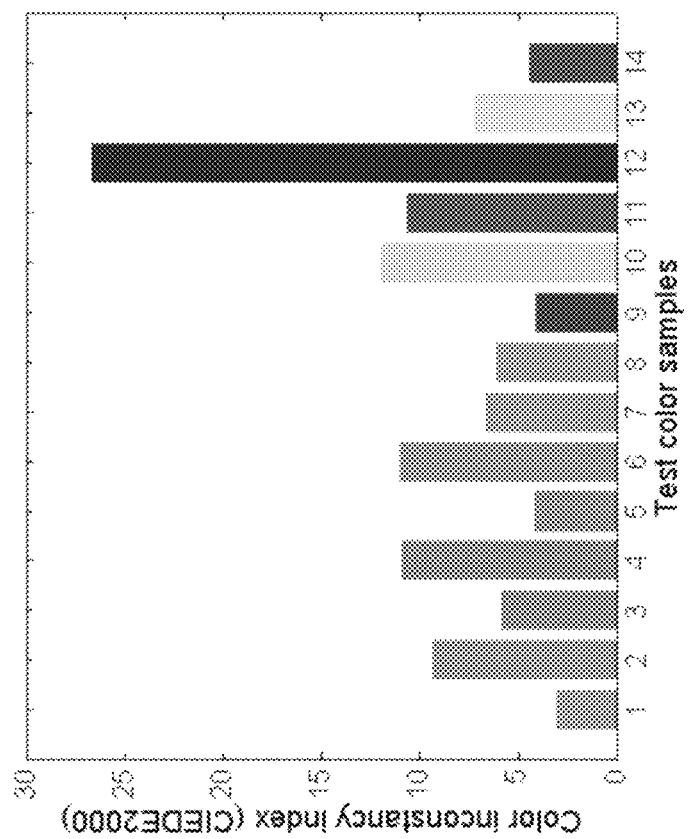

The illuminant in FIG. 8B contains 4 LEDs with chromaticity coordinates (0.4370,0.4042), corresponding to a CCT of ~3200 K. Its melanopsin contrast is 30.1%, and its maximum-to-minimum melanopsin response ratio is 1.86. The CRI values of its minimum and maximum spectra are 65 and 80. Its CQS values are poorer and range from 37 to 68, and the mean CII for 14 TCSs is 8.2. The CII for TCS 12 is 26.7, more than twice the second largest value of 12.0, for TCS 10 (FIG. 8D).

In examining TCSs, we applied a TCS constraint matrix to mimic changes in the appearance of a simulated environment as the light oscillates from the minimum-melanopsin spectrum to maximum-melanopsin spectrum. The TCS constraint matrix was used to limit the amount of change that occurs to the cones in the eyes of a subject, if the subject were to be looking at a colored object under the modulated light herein. TCS refers to test color samples that were chosen as commonly representative samples of colored objects we might encounter in our rooms. The TCSs where chosen because they represent the colors highly encountered in the lighting practice for calculating CRI, which is one of the most important lighting metrics. With the constraint matrix, we were able to specify that, when looking at a TCS, we can only allow our cone responses to change a certain amount, while the algorithm of the techniques herein calculates the optimum melanopsin contrast or optimum range for melanopsin contrast per the TCS matrix value constraints.

However, for viewers suffering SAD or other conditions arising from poor ipRGC stimulation, the therapeutic benefits of a high melanopsin contrast might take priority over color inconstancy, i.e., these individuals may be willing to tolerate subtle changes in the shades of objects in exchange for better therapeutic effects from their interior lighting. It is believed that these subtle shifts can be reduced by using a light source that alternates between the maximum and minimum spectra in a smooth, sinusoidal fashion. Whereas existing light therapies (which use intense steady light) are inefficient and require prolonged dedicated viewing, incorporating phototherapy into general lighting would circumvent such inconvenience, allowing users to receive therapy while engaging in normal daily activities.

Figure 8C:
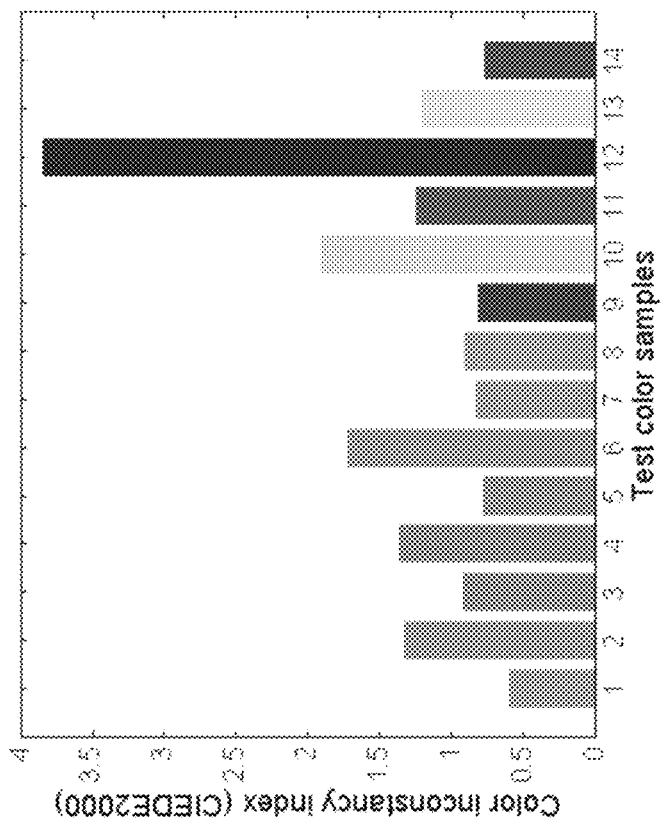
Figure 8F:
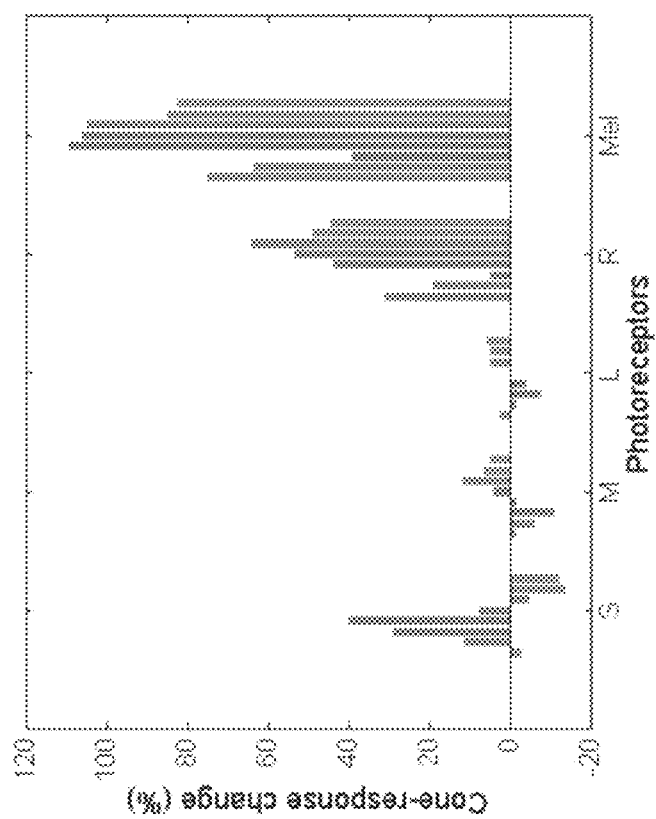
Figure 8E:
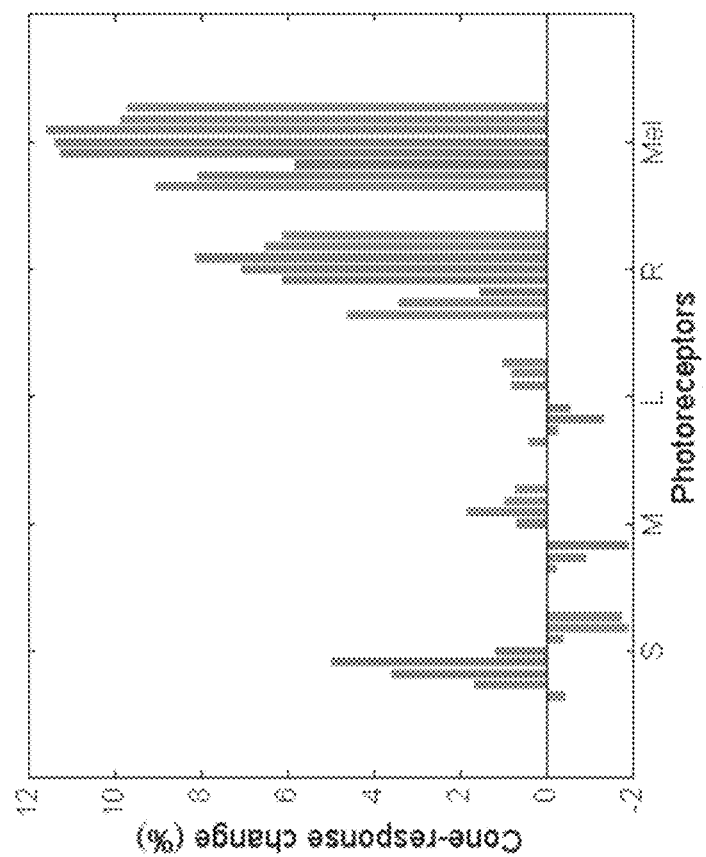
Figure 10B:
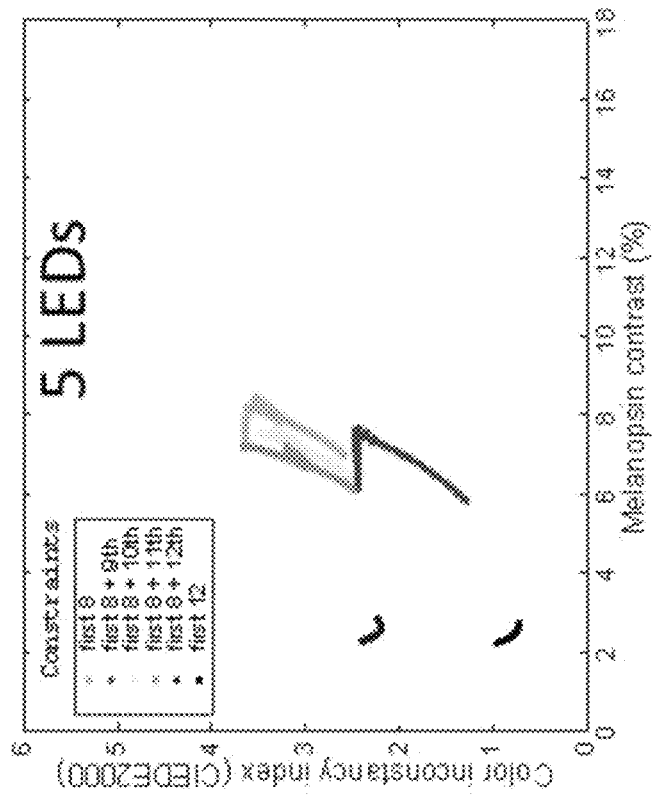
FIGS. 10A-10E illustrate mean CII vs. melanopsin contrast as TCS boundary conditions are expanded for lights with 4, 5, 6, 10, and 400 independent LED channels, respectively.
Figure 10A:
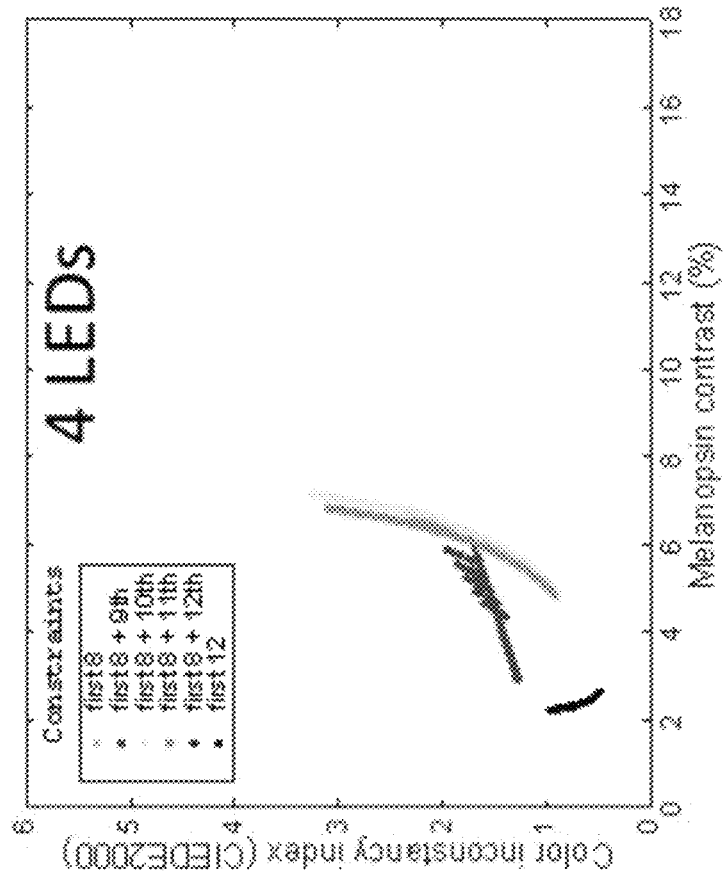
Figure 10D:
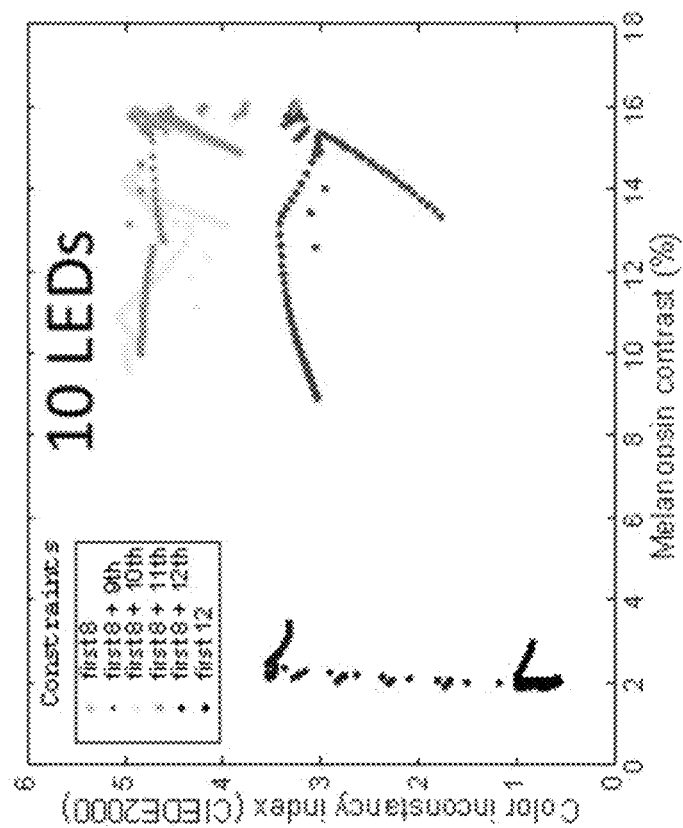
Figure 10C:
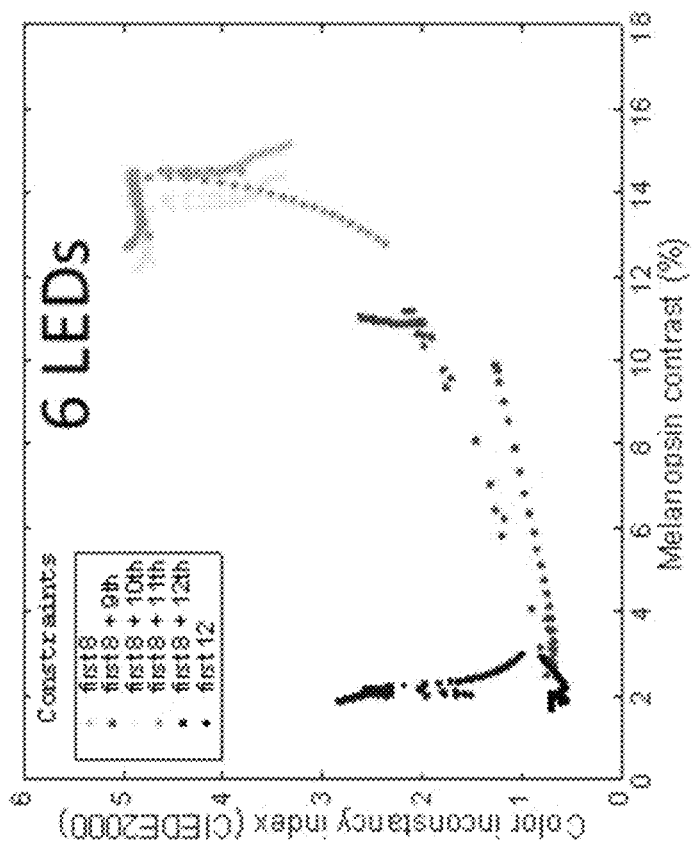
Figure 10E:
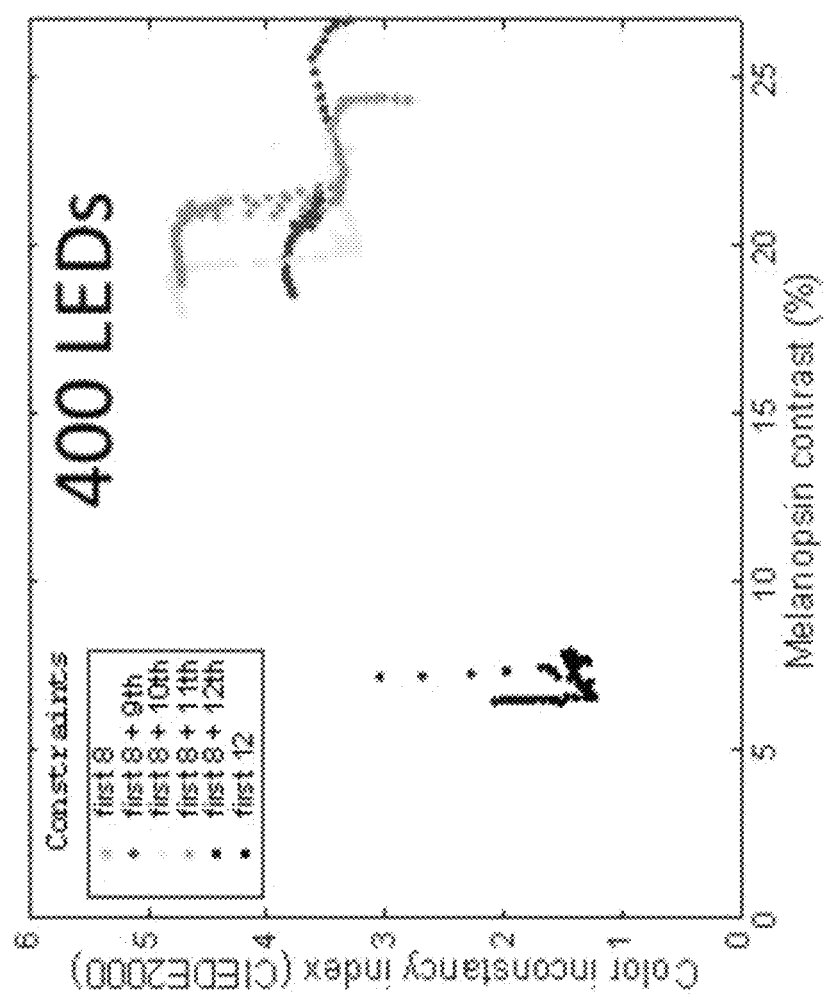

A small tolerance in visual shift usually leads to a low CII. In combination with a large FWHM, the light source can produce a moderate melanopsin contrast with hard-to-notice oscillation. Recent in vitro recordings suggested that the optimal modulation frequency for melanopsin-based photoresponses in rat ipRGCs was ~0.1 Hz (FIG. 4). Hence even with the worst case scenario, such as a room dominated by the color similar to TCS 12 (deep blue), the change generated by a light source oscillating sinusoidally at ~0.1 Hz will be slow and likely barely noticeable. For example, a 4-LED system with a 100 nm FWHM (FIG. 8A) yields a high CRI of 92. The CII mean for all TCSs is 1.6 (FIG. 8C). This system has a melanopsin contrast of 4.2%. A 5-LED system can give a slightly higher contrast of 6.4%, but also a higher CII of 3.

Any single simulation will not account for or control for all the possible contrast effects that can arise in daily experience. Ultimately, the near-infinite number of environments with their unique geometries, object arrangements, and interplay with outdoor lighting provide for a near-infinite range of lighting situations. Observer variability adds an additional confounding factor.

While we have used example color appearance models to assess dynamic lighting changes in determining appropriate light modulation models, other color appearance models may be used. For example, the recent CIE color appearance model, CIECAM02, could be used, although environmental variability may limit the usefulness of that model. CIECAM02, for example, provides a streamlined and effective means to describe color appearance with respect to scene context, but would require known background and surround conditions.

Other factors may also be applied when determining an appropriate light modulation model for producing dynamic light. Mesopic visual response may be considered, for example. Mesopic visual responses become relevant at lower lighting levels. The melanopsin contrast optimization algorithm described above does not consider rod responses whatsoever, as rods are likely saturated or nearly saturated under our dynamic lighting. Utilizing a more complicated model that takes into account mesopic vision could be achieved using the Hunt (R. W. G. Hunt: The Reproduction of Colour (Fountain Pr., England, 1995) 5th ed., Chap. 31, p. 705) model, for example. Adding rod response to the present models would add to the list of constraints and may reduce melanopsin contrast. The model could use even further, more advanced illuminant designs where the color coordinates of the illuminant itself are allowed to vary. The motivation would be to reduce the just noticeable differences (JNDs) in color sample tests to below threshold. A consideration with such models is that a favorable shift in JND for one color may be offset by unfavorable shifting for other colors. There are numerous contrast phenomena, which could take place based on the arbitrary arrangements of objects, such as simultaneous contrast and crispening effects. Ultimately, quantifying true melanopsin contrast would be best achieved using an accurate assessment of contrast not only from the direct illuminant itself, but the summation of all reflections in a given environment. Therefore the modulation model could be adapted to consider such reflection effects, partly or in total. However, generally speaking some self-restraint from over-modeling allows for conceptual and computational simplicity, while being no less accurate on balance than a highly refined simulation when it comes to general modeling.

While these additional factors can be implemented in producing the light modulation models herein, in exemplary embodiments, the broader approach described above is used to produce dynamic light (i.e., dynamic illumination). As discussed herein, we observed general trends through statistical analysis of the data.

We observed that more LEDs will provide more contrast, but more LEDs can lead to more instability in color appearance as a high proportion of simulation states, causing an increase in CII as well as larger changes in CRI and CQS. CII, as well as CRI, CQS, and other light quality metrics and indices, can be used to provide further constraints in selecting the light modulation modes that provide the best utility. In the case of CII, constraining below a certain value for test color sample and/or environmental objects calculations may be desirable. In the case of light quality indices, a limit in the change in index value between the light modulation modes may be desirable.

Therefore, in some examples, we counteract the instability by decreasing the independence of the LED channels by broadening the spectral width of each LED. Surprisingly, spectral broadening does not impact the contrast values significantly. Programming a narrow cone-change tolerance range (say ±5%) to TCS into the algorithm limits permitted contrast values to levels below those which result from spectral broadening—up to FWHM values as high 50 nm. The benefit of large spectral width was demonstrated in our general lighting example. In practice, large FWHM can be obtained from LED chips of relatively low quality. If needed, phosphors can be incorporated into the lighting design.

In exemplary embodiments, only three metrics may be assessed: melanopsin contrast, color fidelity and/or quality, and constancy of scene appearance. Using four or more independently controlled LED channels, an optimization model has been presented to maximize melanopsin contrast while maintaining good quality for color rendering and color temperature. For example, a moderate melanopsin contrast of 5% can be achieved with excellent CRI and CII. Such a light source could replace existing interior lighting to improve well-being and productivity.

As seen from the considerable spread in outputs, even when correlations are relatively high, our method benefits from a large number of iterations from which one can cherry-pick the combination of system traits providing the best contrast, constancy, and color rendering. Furthermore, the methods herein may control for nonlinear outputs such as CRI and CII in addition to contrast during 7. For example, the techniques herein may use null space analysis and subspace optimization, using a model to conduct calculus of several variables and find extrema with respect to variables. The techniques may use manifold analysis of the hyperspace of x,y-doublets which overlap in chromaticity space.

The dynamic (modulated) lighting described herein could prove especially advantageous in settings with a general lack of sunlight, such as settlements in and around the Arctic Circle where winters can be almost entirely devoid of light, and inside submarines. Dynamic lighting would also be beneficial at work and school where alertness and productivity is key. Environments such as factories could rely on such lighting to boost productivity or maintain alertness in order to minimize workplace injury.

We have empirical data suggesting that the melanopsin-specific dynamic light enhances alertness and cognitive performance in human subjects. FIG. 11 illustrates human EEG recordings obtained using the 5-channel light source. To generate a melanopsin-selective oscillation, the combined emission spectrum alternated smoothly between a state that weakly stimulates melanopsin ("min" in FIG. 11) and another that stimulates melanopsin more strongly ("max"). Both states excite cones almost equally, and fully saturate rods; thus, the oscillation between the two states specifically targeted melanopsin. The resulting dynamic light had a comfortable warm white hue and appeared remarkably constant to the observer. These EEG data suggest that this subconsciously flickering light increases alertness significantly more than steady light. In the test of FIG. 11, we objectively quantified the subjects' alertness by measuring EEG frequencies in the low alpha range, as researchers have found that a decrease in power within this range is correlated with an increase in alertness. The slowly flickering stimuli (0.01 Hz and 0.1 Hz) tended to reduce low-alpha signals more than the other stimuli, including the "max" steady light which emitted more photons than the flickers, suggesting that melanopsin-targeted flickering light promotes alertness better than steady light. In another human study, summarized in FIG. 12, we used a computer-based test to evaluate cognitive performance under either the 5-LED light delivering a melanopsin-selective oscillation, or the 5-LED light held steady either at the minimum-melanopsin state or the maximum-melanopsin state. Results showed that under the melanopsin-selective oscillating light, the subjects completed the cognitive test with shorter reaction times, a lower distractability, and lower error rates.

Figure 13:
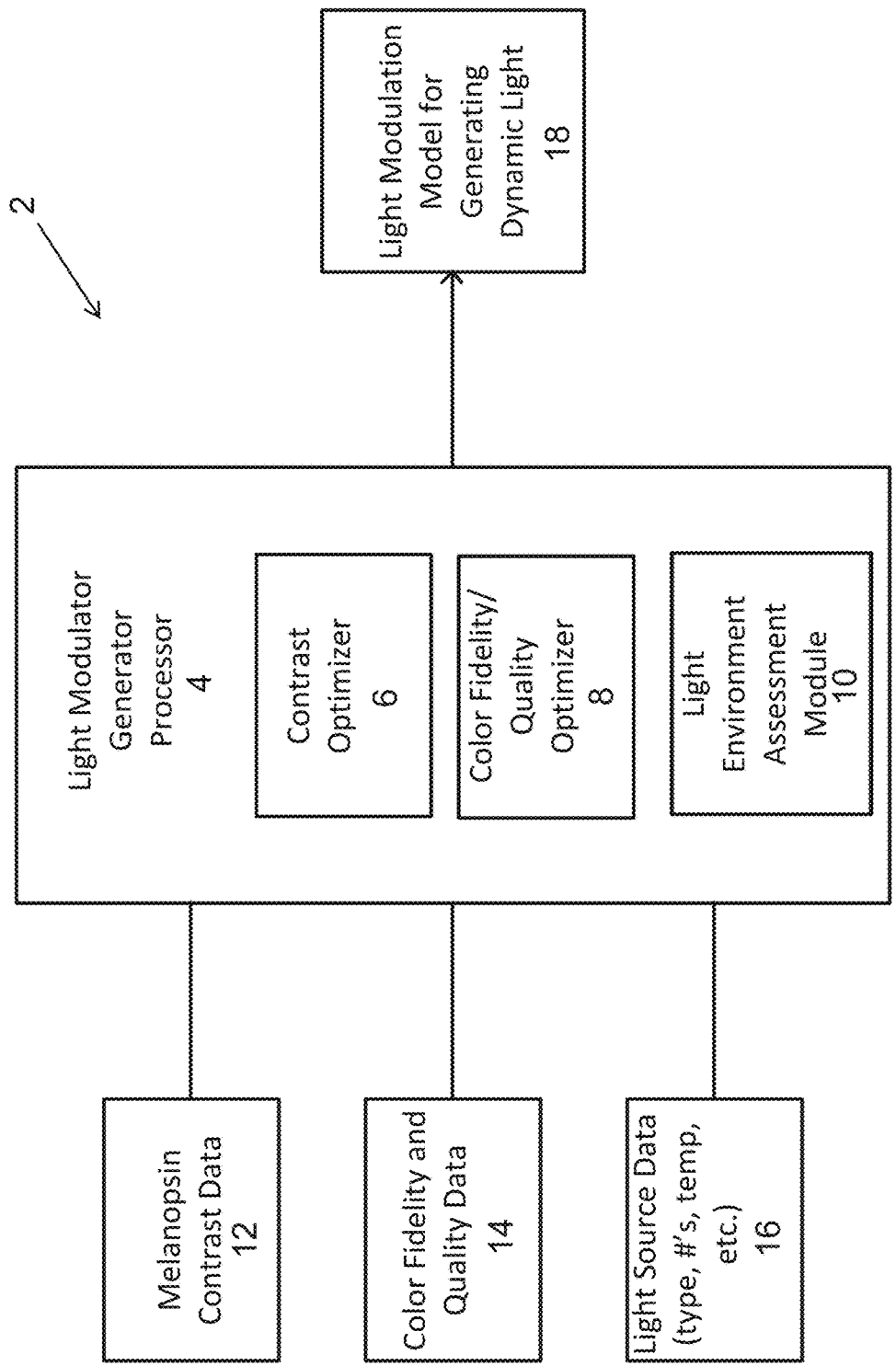
FIG. 13 illustrates a processing system for generating light modulation models and controlling light output to produce dynamic light, in accordance with examples described above.

FIG. 13 illustrates a processing system 2 for generating light modulation models and controlling light output to produce dynamic light, in accordance with examples described above. Melanopsin contrast data 12 and color fidelity and quality data 14 are provided to a light modulation model generator 4, formed of a processing device having one or more processors executing non-transitory instructions stored on one or more processor readable memories also within the processing device. Optionally, light source data 16, such as the type of light source (LED or other), the total number of LEDs available for using in the model, the color output of the LEDs, a color temperature data, including environmental color temperatures for the ambient space to be illuminated, may be provided to the processing device. The processing device includes a melanopsin contrast optimizer 6, a color fidelity optimizer 8, and a light and lighting environment assessment module 10. The processing devices generate a light modulation model 18 which may be a set of modulation instructions in an executable format, whether digital data or analog data, that will be used to modulate light from the light source.

Figure 14:
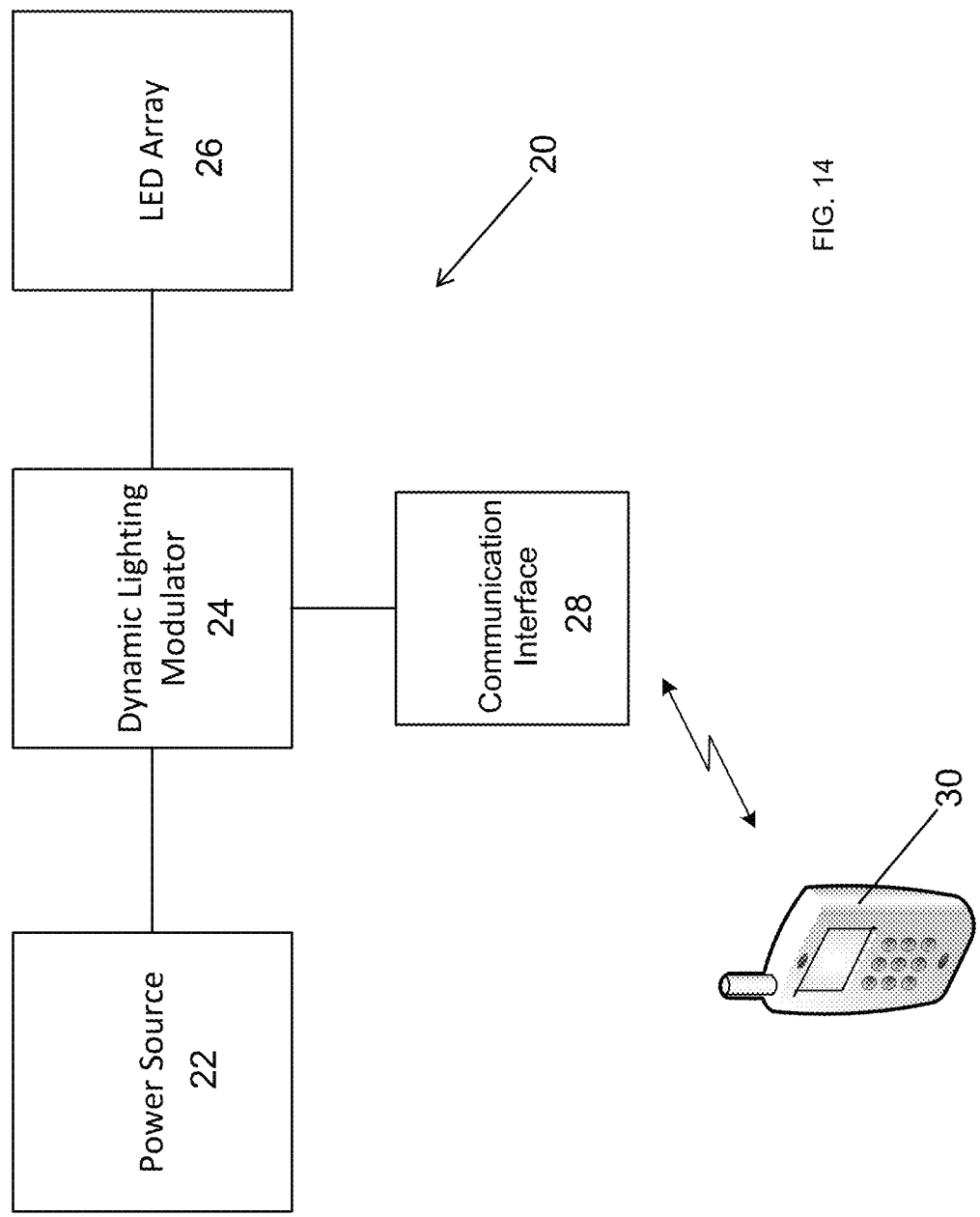
FIG. 14 illustrates an example implementation of the generated light model in an LED light formed of an LED array.

FIG. 14 illustrates an example implementation of the generated light model 20 in an LED light formed of an LED array 26. Here, LED array refers to any light source having one or more LEDs. A power source 22 provides light control signals to a dynamic lighting modulator 24 that stores the light model and that provides modulation instruction signals to the LED array 26 to modulate the light in accordance with that determined through the techniques described herein. Optionally, the light source may include a communication interface 28 coupled to the dynamic lighting modulator 24 to allow for communication with a separate control device 30, such as a handheld computer, for modifying light modulation model data stored in the dynamic lighting modulator 24.

Figure 15:
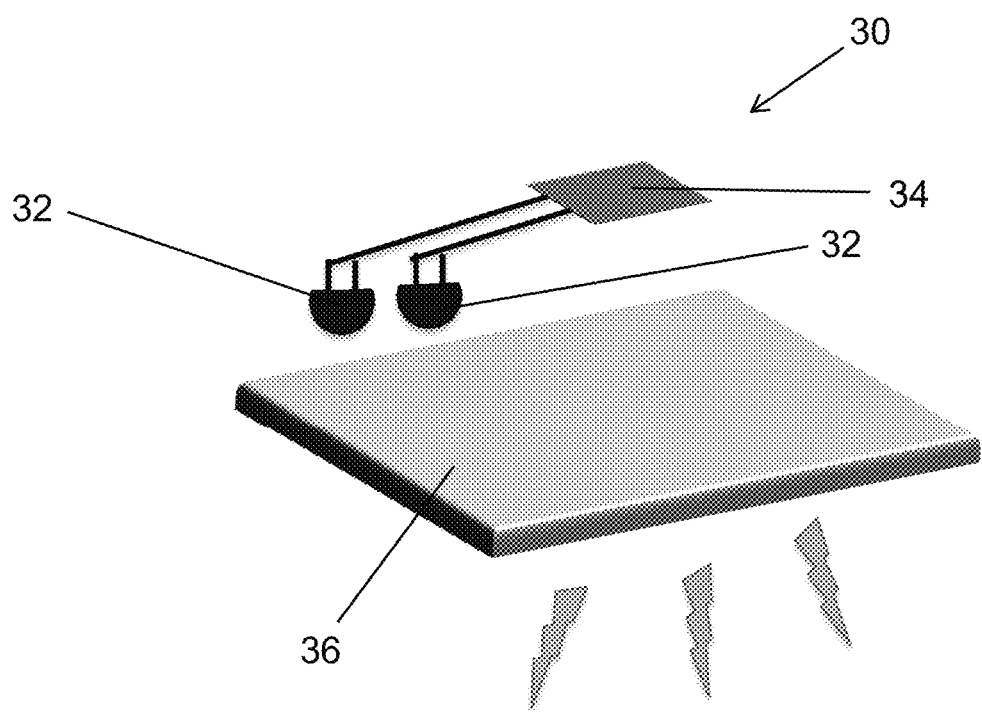
FIG. 15 is an example of a flat panel display device having two LEDs electrically connected to a light controller providing modulating light signal controls to the LEDs, and with a diffuser panel for evenly emitting light.

FIG. 15 is an example of a flat panel display device 30 having two LEDs 32 electrically connected to a light controller 34 providing modulating light signal controls to the LEDs, and with a diffuser panel 36 for evenly emitting light.

Figure 16:
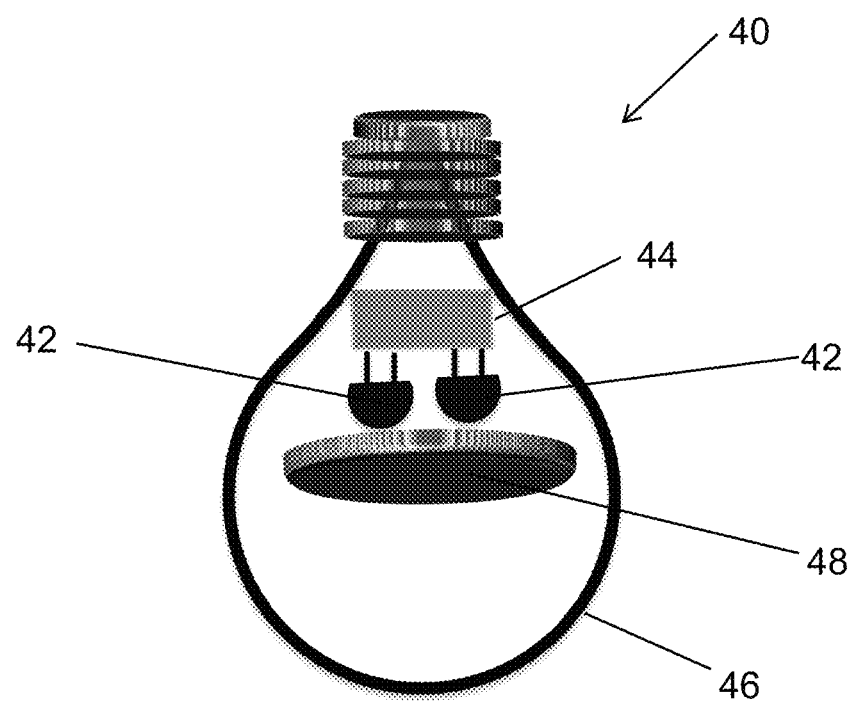
FIG. 16 is an example of an Edisonian lighting configuration in which two LEDs electrically connected to a light controller providing modulating light signal controls to the LEDs, are housed within a light bulb shaped housing and in which a diffuser panel is shown.

FIG. 16 is an example of an Edisonian lighting configuration 40 in which two LEDs 42 electrically connected to a light controller 44 providing modulating light signal controls to the LEDs, are housed within a light bulb shaped housing 46 and in which a diffuser panel 48 is shown.

FIG. 17 illustrates an exemplary method 100 of adapting a pulsed light for general illumination. At box 102, the method 100 comprises providing a plurality of LED channels each generating light, the LED channels including at least four distinctly colored LEDs. At box 104, the method 100 comprises setting a first light mode at a first spectrum to maximally stimulate melanopsin responsiveness of a subject, the first spectrum being formed by light from the at least four distinctly colored LEDs, the first light mode having a light intensity that maximizes melanopsin contrast responsiveness and having a blue light intensity, a red light intensity, and/or a green light intensity that define a color temperature and brightness of the first light mode. At box 106, the method 100 comprises setting a second light mode at a second spectrum to more weakly stimulate melanopsin responsiveness of the subject compared to the first light mode, the second spectrum being formed by light from the at least four distinctly colored LEDs, the second light mode having a light intensity that more weakly stimulates melanopsin responsiveness and having a blue light intensity, red light intensity, and/or a green light intensity that define a color temperature and brightness of the second light mode. At box 108, the method 100 comprises setting the color temperature and brightness of the first light mode to match the color temperature and brightness of the second light mode. At box 110, the method 100 comprises modulating between the first light mode and the second light mode to stimulate the subject while maintaining an optimized melanopsin contrast between the first light mode and the second light mode.

Maintaining an optimized melanopsin contrast between the first light mode and the second light mode may include maximizing the melanopsin contrast between the first light mode and the second light mode. Each of the first light mode and the second light mode is characterized by a correlated color temperature (CCT) and brightness, and the method may further include iteratively setting the first light mode and the second light mode over a CCT from 3000 to 11000 K in intervals, and modulating between the first light mode and the second light mode each iteration. The method may further include determining whether the first spectrum and the second spectrum induce a change in cone response from test color samples within a maximum acceptable cone response change range. The method may further include determining whether the first spectrum and the second spectrum induce a change in cone response from test color samples within a maximum acceptable cone response change range.

Additionally, the method may include determining whether the first spectrum and the second spectrum induce a change in cone response from test color samples within a maximum acceptable cone response change range. The method may include configuring the first spectrum and the second spectrum to be cone metamers by applying a mathematical optimization algorithm with constraints. If the first spectrum and the second spectrum induce a change in cone response from test color samples, the method may include calculating a color inconstancy index (CII) of the first spectrum with respect to the second spectrum and, if the value of the CII between the first spectrum and the second spectrum is greater than a maximum acceptable CII value, adjusting the first spectrum and/or the second spectrum until the value of the CII given the first spectrum and the second spectrum is within an acceptable CII value. Similarly, if the first spectrum and the second spectrum induce a change in cone response from test color samples, the method may include calculating light quality indices of the first spectrum and of the second spectrum and calculating a difference between the light quality indices of the first spectrum and the second spectrum and, if the difference is greater than a maximum acceptable light quality index change, adjusting the first spectrum and/or the second spectrum until the difference is less than or equal to maximum acceptable light quality index change. Calculating light quality indices may include calculating a Color Rendering Index (CRI) and/or a Color Quality Scale (CQS) and/or a Michelson contrast and/or a Weber contrast.

The techniques herein may be used in any number of lighting configurations and light applications. For example, the modulated light techniques may be used for therapeutic lighting, in which light is modulated to a desired amount having the largest therapeutic effect on a subject or group of subjects. Subjects may be provided a series of different modulated light conditions, for example, at different wavelengths and using different combinations of different-wavelength emitting LEDs, and different numbers of LEDs. From there, an optimum therapeutic modulated light model may be developed for use with the subject. In some examples, that light model may be programmed into automated lighting systems, such as wirelessly-enabled lighting solutions in the home, whereby the model can be applied to the lighting when the presence of the subject has been detected. An example of such therapeutic lighting could be deployed for seasonal affective disorder (SAD).

The lighting module can be one that affects the lighting in the home, work space, commercial space or other on an ongoing basis or at particular times of the year, as with SAD.

The light modulation techniques herein may be incorporated into displays by modulating light, and more particularly part of the display screen image or even the overall color space of a display, to increase the responsiveness of a subject. Indeed, with a control display, such as computer screen or handheld device screen, tests can be given to subjects while simultaneously adjusting modulating lighting conditions to assess optimum conditions for a subject. Those tests could be productivity tests, alertness tests, drowsiness tests, response time tests, or any number of other measurable metrics of brain activity that might be affected by lighting conditions.

In yet other examples, the techniques may be used for overall light mixing, such as use in fiber optics for mixing of different LED light, for display or data communication purposes.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or that are permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or by processor-implemented hardware modules. The performance of certain of the operations may be distributed among the one or more processors, not only residing within a single machine (having different processing abilities), but also deployed across a number of machines. In some example embodiments, the processors may be located in a single location (e.g., deployed in the field, in an office environment, or as part of a server farm), while in other embodiments the processors may be distributed across a number of locations.

Unless specifically stated otherwise, discussions herein using words such as "processing," "computing," "calculating," "determining," "presenting," "displaying," or the like may refer to actions or processes on a GPU thread that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A method of generating light using a light source, the method comprising:
    generating lighting signals for controlling the light source, wherein the light source is configured to produce a plurality of distinct colors in generating the light, at least one of the distinct colors falling within a blue spectral light band;
    modulating the lighting signals to modulate the light produced by the plurality of distinct colors, the modulation being chosen by a lighting controller to repetitively provide alternating light pulses of a first distinct color within the blue spectral light band and of a second distinct color within the blue spectral light band, the alternating light pulses oscillating sinusoidally between the first distinct color and the second distinct color at a frequency between 0.05 and 0.15 Hz, the first distinct color being closer to 480 nm than the second distinct color, and the modulation being chosen to maintain color temperature and color quality of the light within an acceptable range during the alternating light pulses of the first distinct color and the second distinct color; and
    applying the modulated lighting signals to the light source and generating the light for thereby increasing the melanopsin contrast responsiveness of the subject exposed to the light,
    wherein modulating the lighting signals to modulate the light produced by the plurality of distinct colors comprises applying the modulation to maintain color rendering within a predetermined range.

2. The method of claim 1, wherein the color rendering is a Color Rendering Index (CRI) and/or Color Quality Scale (CQS) and the predetermined range for the color quality corresponds to having a CRI and/or CQS value of above 60.

3. The method of claim 2, wherein the predetermined range for the color quality corresponds to having a CRI and/or CQS value of above 70, 80, or 90.

4. The method of claim 2, wherein the predetermined range for the color quality corresponds to having a CRI and/or CQS value of above 90.

5. The method of claim 2, wherein the predetermined range for the color quality corresponds to having a CRI and/or CQS value of above 95.

6. The method of claim 1, wherein the light source is an LED light source.

7. The method of claim 6, wherein the LED light source is an LED array comprising a plurality of LEDs.

8. The method of claim 6, wherein the LED light source comprises 4 or more LEDs.

9. The method of claim 6, wherein the LED light source comprises 5 or more LEDs.

* * * * *